(12) United States Patent
Harada

(10) Patent No.: US 6,984,835 B2
(45) Date of Patent: Jan. 10, 2006

(54) IRRADIATION APPARATUS AND IRRADIATION METHOD

(75) Inventor: Hisashi Harada, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 140 days.

(21) Appl. No.: 10/762,244

(22) Filed: Jan. 23, 2004

(65) Prior Publication Data

US 2004/0213381 A1  Oct. 28, 2004

(30) Foreign Application Priority Data

Apr. 23, 2003 (JP) .............................. 2003-118801

(51) Int. Cl.
  *H01J 37/09*  (2006.01)
  *A61N 5/00*  (2006.01)
  *G21K 1/04*  (2006.01)

(52) U.S. Cl. .............................. 250/505.1; 250/515.1; 250/503.1; 250/492.3; 313/359.1; 378/65; 378/147

(58) Field of Classification Search ............. 250/505.1, 250/515.1, 503.1, 492.3; 313/359.1; 378/65, 378/147
See application file for complete search history.

(56) References Cited

U.S. PATENT DOCUMENTS 6,127,688 A * 10/2000 Wu ........................ 250/505.1
6,600,810 B1 * 7/2003 Hughes ...................... 378/152

FOREIGN PATENT DOCUMENTS

JP            10-151211        6/1998

* cited by examiner

*Primary Examiner*—Nikita Wells
(74) *Attorney, Agent, or Firm*—Leydig, Voit & Mayer, Ltd.

(57) ABSTRACT

An irradiation apparatus has a large irradiation field and is capable of ensuring the uniformity of a dose distribution without strengthening the performance of an irradiation field enlarging device. The irradiation apparatus includes a beam interruption part for performing a plurality of irradiations of a radiation beam, a position control part for controlling a location to be irradiated in such a manner that the entire surface of the target can be irradiated in a plurality of irradiation zones including an overlapping area formed by the plurality of irradiations, and a multileaf collimator control part for providing a slope to a dose distribution in the overlapping area of the respective irradiation zones, so that the dose distribution over the entire surface of the target including the overlapping area is made flat or uniform by the plurality of irradiations of the radiation beam.

15 Claims, 24 Drawing Sheets

FIG. 19
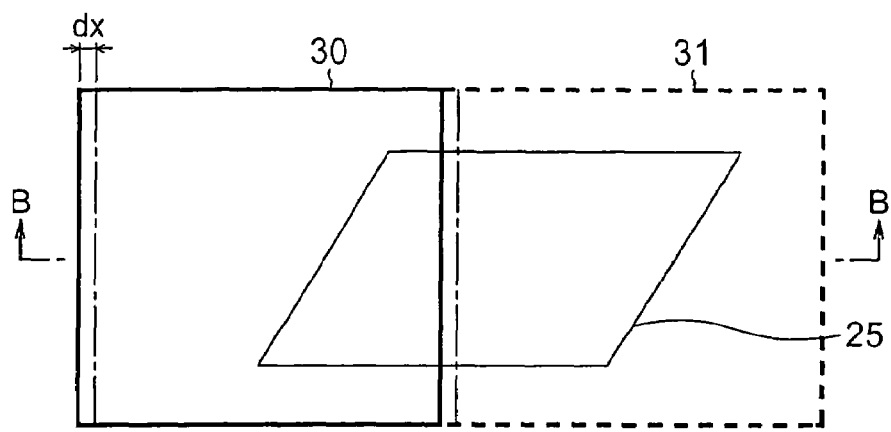
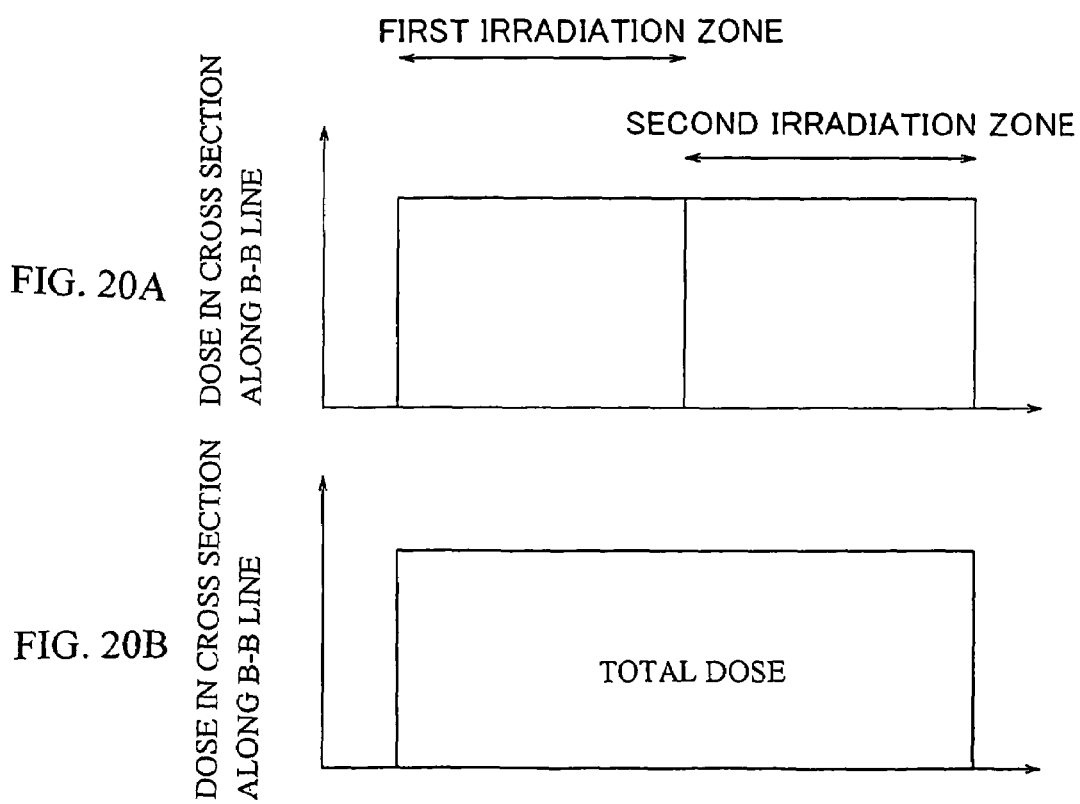
FIG. 20A
FIG. 20B

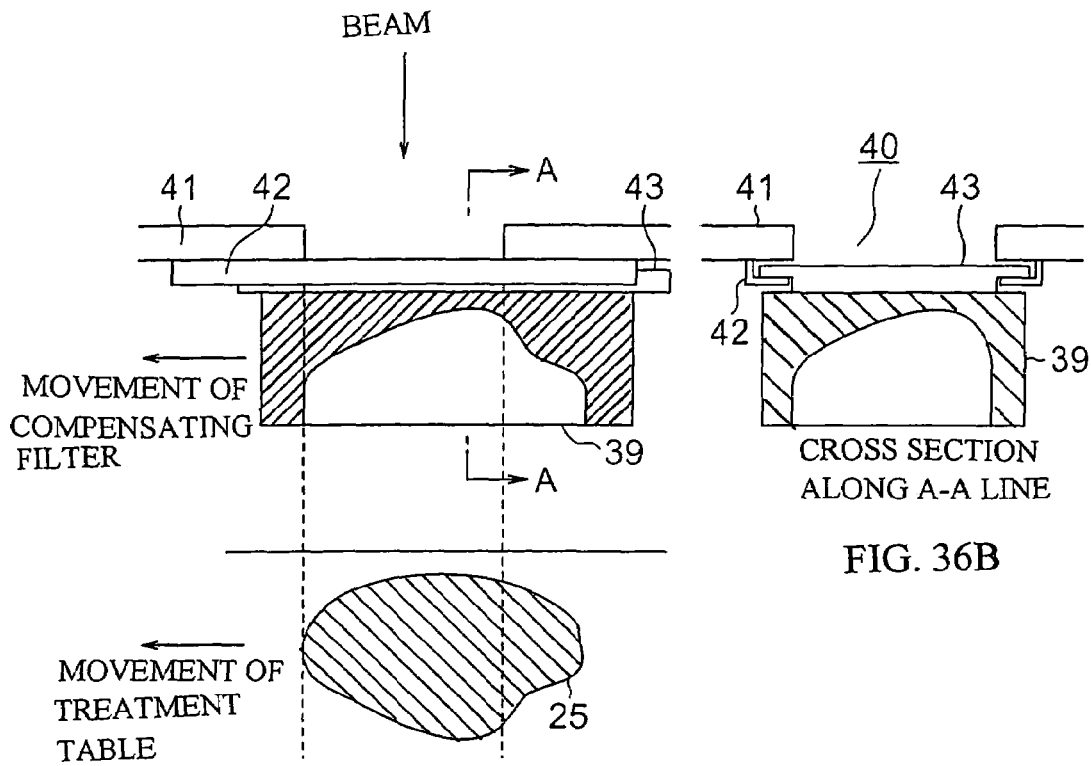
FIG. 36B
FIG. 36A
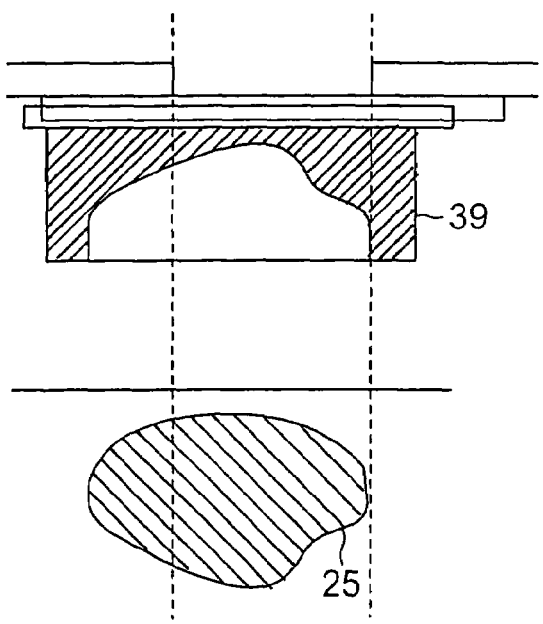
FIG. 36C

IRRADIATION APPARATUS AND IRRADIATION METHOD

BACKGROUND OF THE INVENTION

1. Field of the Invention

The present invention relates to an irradiation apparatus for irradiating particle beams or corpuscular rays to a location to be irradiated as well as an irradiation method using this apparatus.

2. Description of the Related Art

Known methods of enlarging the irradiation field of an irradiation apparatus, which treats cancer by using such a kind of particle beams, generally include a double scatterer method and a Wobbler method. In the double scatterer method, there are arranged two scatterers through which a particle beam passes so that a uniform dose distribution can be formed. On the other hand, in the Wobbler method, a particle beam is irradiated on a scatterer while being moved in a circle by means of an electromagnet so that a uniform dose distribution can be formed in the vicinity of the center of the circle. The field of irradiation thus obtained is usually of an area of from about 15 cm×15 cm to about 20 cm×20 cm, which is sufficient for irradiation of a spot or location to be treated in a lot of cases (for instance, see a patent document: Japanese patent application laid-open No.H10-151211).

However, there may also be some cases requiring irradiation fields larger than the above-mentioned one. For instance, larger flows are often required for elongated areas such as the oesophagus, the neck of the womb (cervix), and the area from the mandible to the shoulder. In these cases, the shape of a large irradiation field as required is not a square or a circle but a rectangle or an oval of from 15 cm×20 cm to 20 cm×25 cm or larger.

One method of achieving such a large irradiation field, conceives that the distance from an irradiation field enlarging device to a location to be irradiated (hereinafter also referred to as the target) should be increased. However, in this case the rotating gantry used is a heavy structure having a diameter of about 10 m and a weight of about 200 tons, and at the same time it is a precision machine with its center of rotation designed to keep an accuracy of about +1/−1 mm. Thus, it is difficult to further enlarge such a structure even in terms of cost as well as accuracy.

In addition, another method of achieving a large irradiation field is to strengthen the performance of an irradiation field enlarging device. In the Wobbler electromagnet, however, there arises a problem that when the magnetic field strength is increased to generate an alternating magnetic field, ac loss due to the eddy current generated in the iron core of the magnet becomes large, thereby heating the iron core to a high temperature.

Moreover, although a strategy of lengthening the magnetic poles of the electromagnet can be conceived, too, it is undesirable from the viewpoint of keeping the rotating gantry small.

On the other hand, in the case of using the double scatterer method, there is a technique of increasing the thickness of the scatterer to enlarge the irradiation field. In this case, however, beams passing through the scatterer are decelerated therein, so increasing the thickness of the scatterer shortens the range of the beams inside the target. Therefore, there is also a limit to the thickness of the double scatterer to be used. Thus, in order to increase the thickness of the double scatterer and to ensure the beam range inside the scatterer at the same time, it is inevitable to raise the beam energy, thus resulting in a larger particle accelerator.

SUMMARY OF THE INVENTION

The object of the present invention is to provide an irradiation apparatus and method capable of providing a large irradiation field while ensuring the flatness of a radiation dose distribution in the irradiation field without strengthening the performance of the particle accelerator or the irradiation field enlarging device.

Bearing the above object in mind, the present invention resides in an irradiation apparatus for irradiating a radiation beam transported from a particle accelerator to the target that is positioned on an irradiation table. A beam interruption part interrupts the radiation beam, and a position control part controls the position of the irradiation table in such a manner that the radiation beam is irradiated onto the entire surface of the target in a plurality of irradiation zones including an overlapping zone formed by a plurality of irradiations of the radiation beam. A "multileaf collimator control part" controls the radiation beam so as to provide a slope to a dose distribution in the overlapping zone of the respective irradiation zones such that the dose distribution is made flat over the entire surface of the target including the overlapping zone by the plurality of irradiations of the radiation beam.

The above and other objects, features and advantages of the present invention will become more readily apparent to those skilled in the art from the following detailed description of preferred embodiments of the present invention taken in conjunction with the accompanying drawings.

BRIEF DESCRIPTION OF THE DRAWINGS

FIG. 19 is a dose distribution chart in the case where two irradiation zones have no overlapping zone.

FIGS. 20A and 20B are individual and total dose distribution charts, respectively, in the case where there is no slope in the dose distribution in the overlapping zone.

FIGS. 36A through 36C are schematic views showing the movement of the compensating filter of FIG. 35.

DESCRIPTION OF THE PREFERRED EMBODIMENTS

Now, preferred embodiments of the present invention will be described below in detail while referring to the accompanying drawings.

Embodiment 1.

Figure 1:
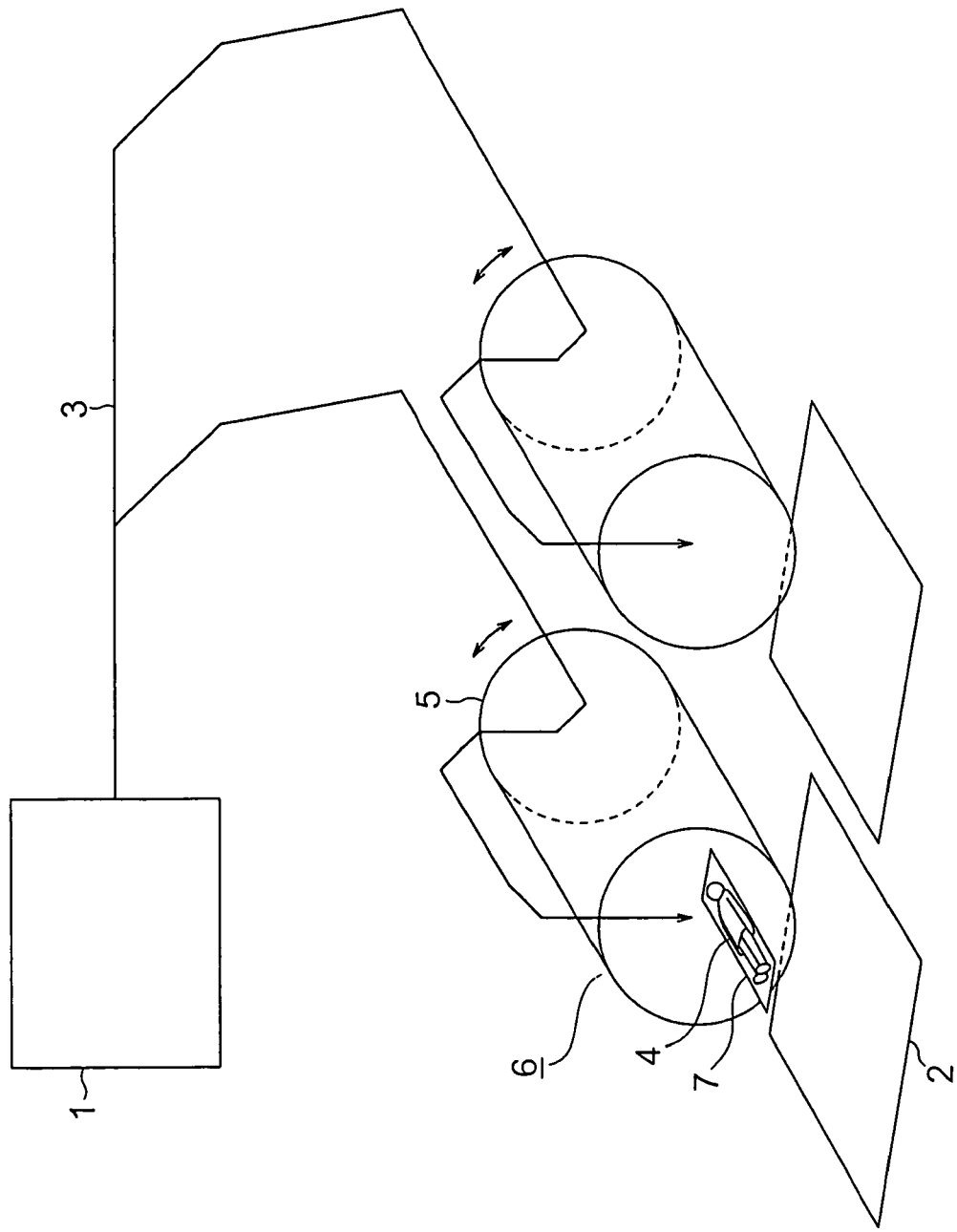
FIG. 1 is a schematic construction view of an irradiation system according to the present invention.
Figure 2:
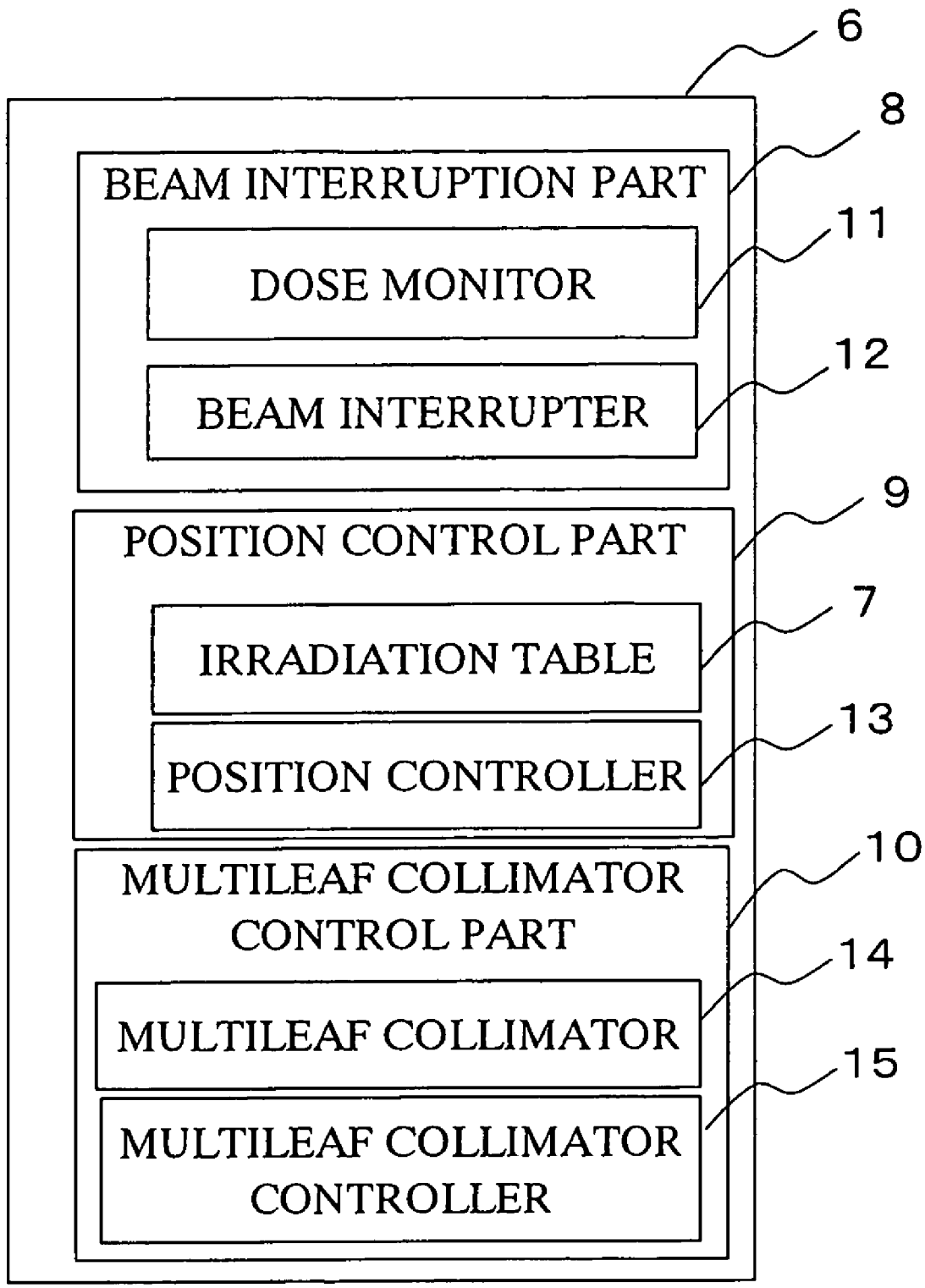
FIG. 2 is a block diagram of an irradiation apparatus of FIG. 1.
Figure 3:
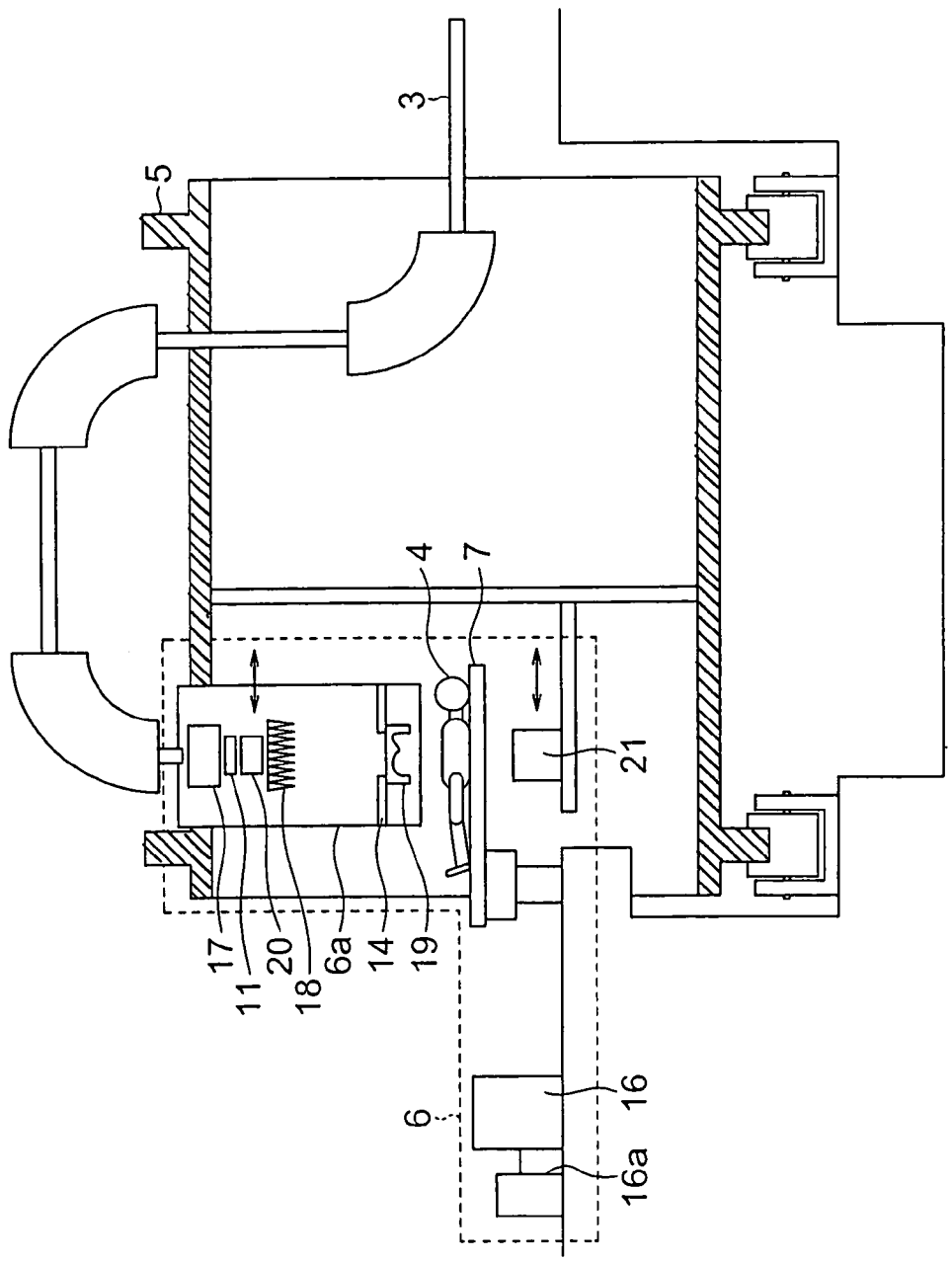
FIG. 3 is a constructional view of a rotating gantry and the irradiation apparatus in the irradiation system of FIG. 1.
Figure 4:
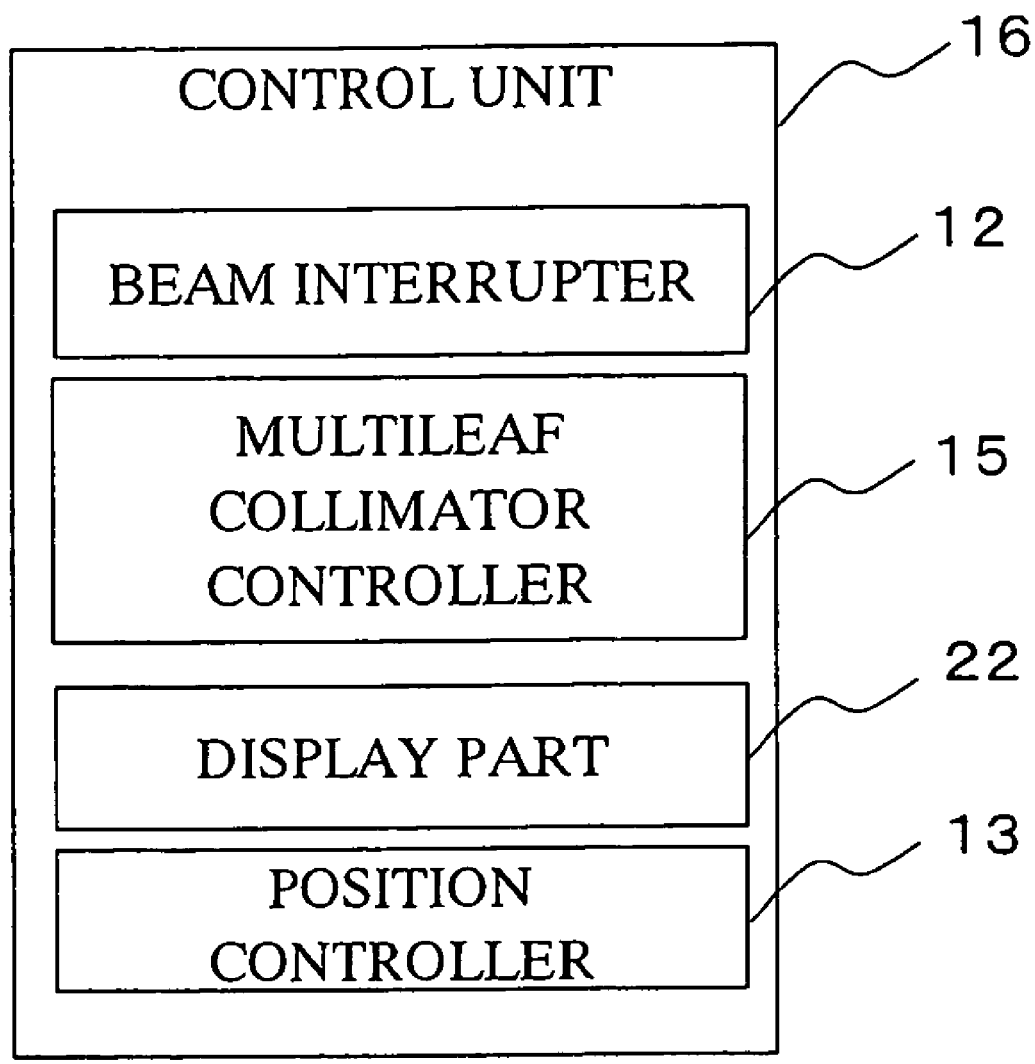
FIG. 4 is a block diagram of a control unit in the irradiation apparatus of FIG. 3.
Figure 5:
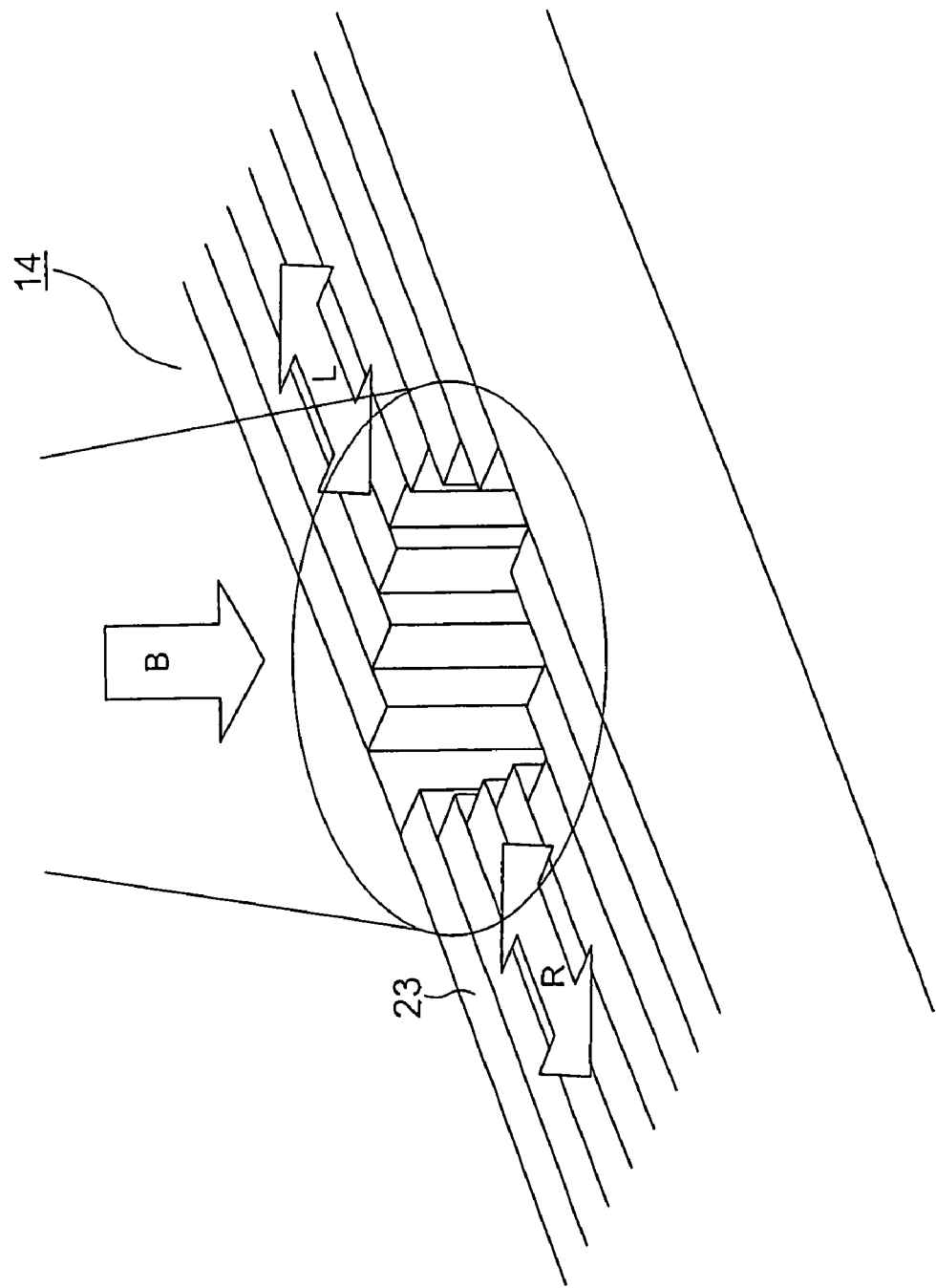
FIG. 5 is a conceptual diagram showing the structure of a multileaf collimator in the irradiation apparatus of FIG. 3.
Figure 6:
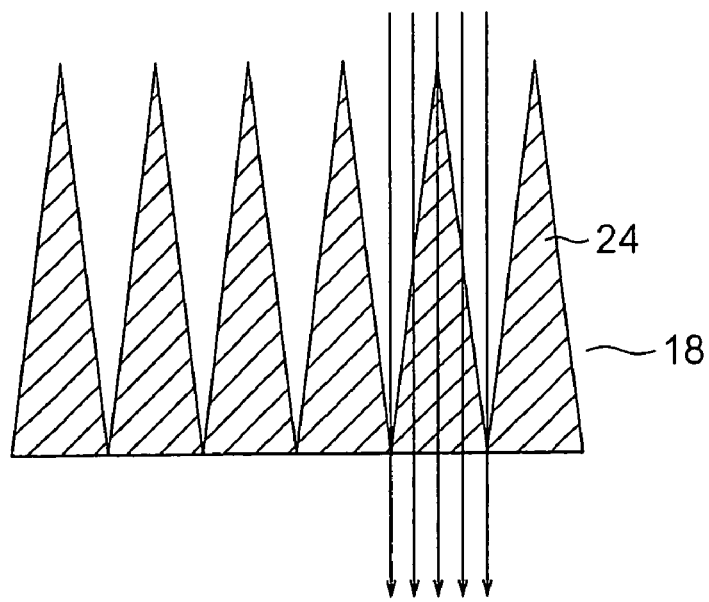
FIG. 6 is a conceptual diagram showing the function of a ridge filter in the irradiation apparatus of FIG. 3.
Figure 7:
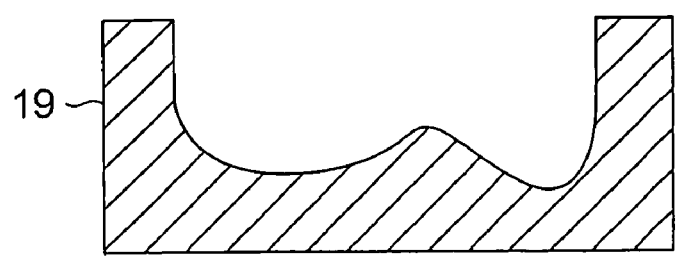
FIG. 7 is a conceptual diagram showing the function of a compensating filter in the irradiation apparatus of FIG. 3.
Figure 7:
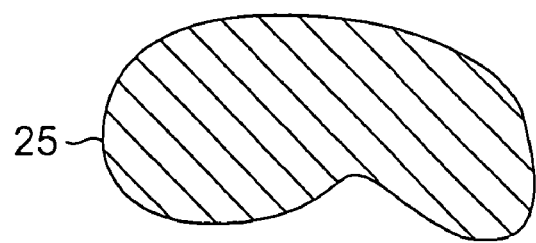

FIG. 1 shows the schematic construction of an irradiation system including irradiation apparatuses constructed in accordance with the principles of the present invention. FIG. 2 is a block diagram that shows an irradiation apparatus in the irradiation system of FIG. 1. FIG. 3 is a constructional view that shows a rotating gantry and an irradiation apparatus in the irradiation system of FIG. 1. FIG. 4 is a block diagram of a control unit in the irradiation apparatus of FIG. 3. FIG. 5 is a conceptual diagram that shows the structure of a multileaf collimator in the irradiation apparatus of FIG. 3. FIG. 6 is a conceptual diagram that shows the structure of a ridge filter in the irradiation apparatus of FIG. 3. FIG. 7 is a conceptual diagram that shows the structure of a compensating filter in the irradiation apparatus of FIG. 3. In the following, the irradiation apparatus will be described as being applied to a radiotherapy apparatus by way of example, but the present invention is not limited to this but is applicable to a variety of irradiation apparatuses.

As shown in FIG. 1, the irradiation system includes a particle accelerator 1 for generating proton beams or carbon beams (C6+) and accelerating them into such an energy spectrum that each beam has a desired range in the body of a patient 4 to be treated, a beam transport system 3 for transporting the beams to respective treatment chambers 2, a plurality of cylindrical rotating gantries 5 provided one for each treatment chamber 2 for changing the directions of irradiation of the beams so that a patient 4 in each treatment chamber 2 can be irradiated by a corresponding beam from a desired direction of the patient 4, and a plurality of irradiation apparatuses 6 for irradiating the beams to the corresponding patient 4. The beam is transported from the particle accelerator 1 to the respective treatment chambers 2 in a finely focused state called the pencil beam. Each patient 4 is fixedly held on an irradiation table 7 in a corresponding treatment chamber 2. In certain cases, fixed beam lines through horizontal ports, vertical ports or the like may be used instead of the rotating gantries 5.

Also, as illustrated in FIG. 2, each of the irradiation apparatuses 6 includes a beam interruption part 8 for performing a plurality of irradiations of a radiation beam, a position control part 9 for controlling the position of the beam in such a manner that the entire surfaces of all locations to be irradiated in a plurality of irradiation zones including overlapping areas formed by a plurality of irradiations, and a multileaf collimator control part 10 for providing a slope to the dose distribution in the overlapping areas of the irradiation zones formed by the plurality of irradiations, so that the dose distribution over the entire surfaces of the locations to be irradiated including the overlapping areas is made flat or uniform by the plurality of irradiations of the radiation beam.

The beam interruption part 8 includes a dose monitor 11 for measuring the amount of dose and interrupting the radiation beam when the dose amount thus measured reaches a predetermined value, and a beam interrupter 12 for controlling the dose monitor 11. The position control part 9 includes an irradiation table 7 that is movable while carrying a patient thereon, and a position controller 13 for moving the irradiation table 7 so that the location of the patient to be irradiated can be adjusted to a desired position which is irradiated by the radiation beam. The multileaf collimator control part 10 includes a multileaf collimator 14 for forming an irradiation area of a desired shape and a desired dose distribution by variably shielding at least part of the radiation beam, and a multileaf collimator controller 15 for controlling the multileaf collimator 14. The multileaf collimator controller 15 controls the multileaf collimator 14 in such a manner that the irradiation zones formed by the irradiations of the radiation beam are shaped into desired configurations, respectively, and a proper slope is given to the dose distribution in each of the overlapping areas of the respective irradiation zones, whereby the dose distribution over the entire surfaces of the locations to be irradiated including the overlapping areas are made flat or uniform by the plurality of irradiations of the radiation beam.

As shown in FIG. 3, each of the irradiation apparatuses 6 also includes an irradiation part 6a, the irradiation table 7, a control unit 16 and a display 16a. Each irradiation apparatus 6 further includes an irradiation field enlarging device 17 for expanding the beam transported by the beam transportation system 3 so as to form an irradiation field, the dose monitor 11 for monitoring the exposure dose of corpuscular radiation included in the irradiation field and automatically interrupting the beam at the time when a prescribed amount of dose has been irradiated, a ridge filter 18 for controlling the dose distribution in the patient's body in a direction along the beam axis, i.e., in the direction of depth, a multileaf collimator 14 for cutting out an irradiation area suitable for treatment by shielding a part of the radiation beam, a compensating filter 19 for adjusting the range of the beam, an X-ray tube 20 for generating X rays, and an image intensifier 21. The image intensifier 21 may be replaced with an X-ray film or another imaging system.

The control unit 16 includes a beam interrupter 12 for controlling the interruption of the beam by controlling the dose monitor 11, a multileaf collimator controller 15 for controlling the multileaf collimator 14 so as to form an irradiation area suitable for treatment in the locations to be irradiated, a display part 22 for processing an X-ray transmission image obtained from the image intensifier 21 thereby to display it on the display 16a, and a position controller 13 for controlling a drive unit that drives the irradiation table 7. The control unit 16 is arranged at a place away from a corresponding treatment chamber 2 so that an engineer or operator can perform adjustments through remote control while observing the display 16a.

The irradiation part 6a creates a uniform dose distribution of the beam within the location or area to be irradiated by the use of the multileaf collimator 14, the irradiation field enlarging device 17, the ridge filter 18 and the compensating filter 19. Usually, the irradiation is planned such that the dose distributions in the respective targets in the location to be irradiated become uniform to within +/−2.5%.

The irradiation field enlarging device 17 comprises a Wobbler electromagnet, a double scatterer or the like as used in the aforementioned conventional apparatus.

The multileaf collimator 14 is composed of a structure called multiple leaves 23, as shown in FIG. 5. The multileaf structure 23 has such quality of material, thickness and structure as to prevent the passage of a beam (see arrow B) therethrough, and have a multiplicity of paired opposing leaves. The respective leaves of the multileaf structure 23 are able to move on a straight line independently of one another (see arrows R and L). Each of the leaves of the multileaf structure 23 is connected with an unillustrated drive unit and an unillustrated position detector for detecting the position of a corresponding leaf. Thus, by remotely controlling the leaves 23 individually, the irradiation zones of arbitrary configurations can be formed in the location to be irradiated. The drive units and the position detectors are controlled by the multileaf collimator controller 15.

The ridge filter 18 is a device comprising a plurality of structural members called ridges 24 being arranged like a washboard as shown in FIG. 6, the thickness of the ridges 24 being changed depending upon its locations. The configuration of the ridges 24 is designed based on detailed calculations. The beam (arrow) passes through the ridge filter 18 of varying thickness after passage of the irradiation field enlarging device 17, whereby it is decelerated in proportion to the thickness of the ridge filter 18. Accordingly, the beam of substantially a single energy spectrum at the upstream side of the ridge filter 18 is turned into one of wide energy spectrum as it passes through the ridge filter 18. Furthermore, since the beam has various angles due to the scattering effect of the ridge filter 18 at the upstream side thereof, the beam with different energy spectrums reaches the patient 4 while its energy spectrums are being mutually mixed with one another at the downstream side of the ridge filter 18.

The compensating filter 19 is called a bolus, as shown in FIG. 7, usually made of polyethylene, etc., and has a shape formed in a manner to adjust the range of the beam to the deepest portion of a target 25 to be irradiated. Therefore, the compensating filter 19 has its shape varied according to the direction in which the irradiation target 25 is irradiated, and hence it is prepared for each portion of the irradiation target 25. The compensating filter 19 is attached to an unillustrated rail-shaped mechanism mounted on the multileaf collimator 14. That is, the compensating filter 19, being fitted to an unillustrated holder beforehand, can be mounted to the multileaf collimator 14 by being caused to slide along the rail-shaped mechanism.

The radiotherapy apparatus has an unillustrated treatment planning device for planning an irradiation treatment. An irradiation plan is prepared for each portion of the target 25 to be irradiated. For preparation of such a treatment plan, the direction of irradiation, the shape of the target 25 to be irradiated, etc., are input from a terminal of the treatment planning device based on the image information obtained by the X-ray computerized tomography (CT) of the irradiation target 25. The treatment planning device automatically calculates, based on the information, the degree of opening of the leaves 23 of the multileaf collimator 14, data for preparing the ridge filter 18 and the compensating filter 19 to be used, etc., and outputs the results to a file. When a radiation beam is irradiated to the target 25 to be irradiated, setting of a corresponding irradiation apparatus 6 is carried out based on this file.

Each irradiation apparatus 6 includes a positioning part for accurately positioning a target 25 to be irradiated with respect to the beam in order to irradiate it with high accuracy. The positioning part is provided with an X-ray tube 20 for generating X rays and an X-ray film or image intensifier 21, and serves to drive the irradiation table 7 by referring to an X-ray transmission image thus obtained. The irradiation table 7 has an unillustrated drive unit for moving the irradiation table in a direction necessary for proper alignment or positioning. An operator can perform proper alignment of the target to be irradiated with respect to the beam by moving the irradiation table 7 through remote control while observing the X-ray transmission image. The positioning accuracy is usually in the range of from 0.5 mm to a few millimeters or so.

Figure 8:
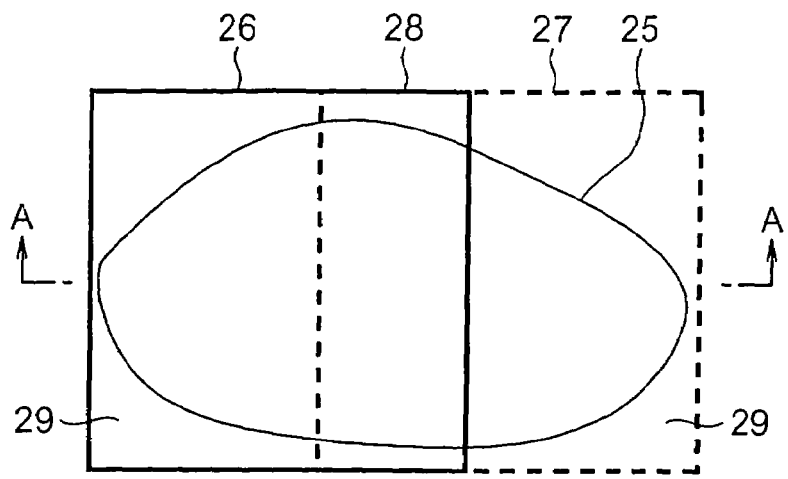
FIG. 8 is a plan view showing an irradiation field in the first embodiment of the present invention.
Figure 9A:
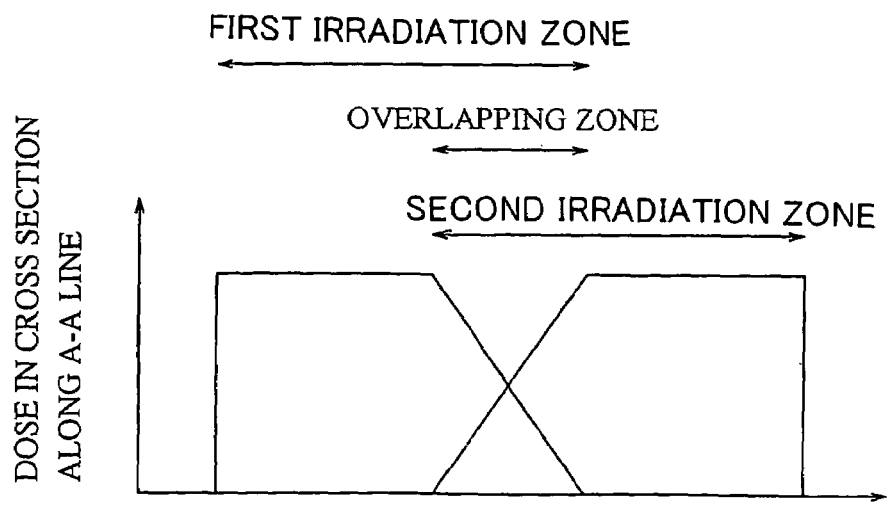
FIGS. 9A and 9B are individual and total dose distribution charts, respectively, showing individual and total doses in respective irradiation zones in cross section along line A—A in the irradiation field of FIG. 8.
Figure 9B:
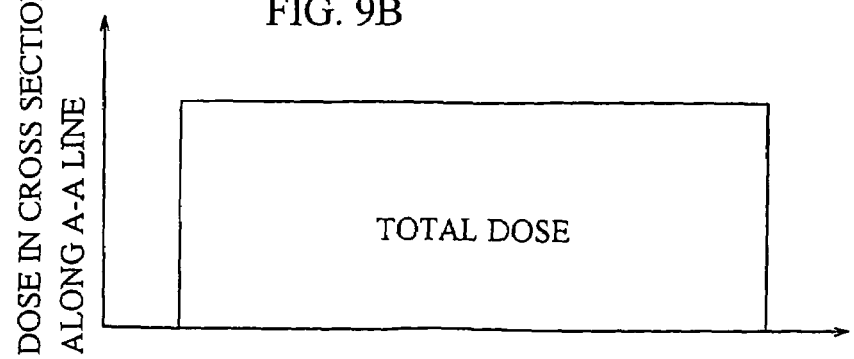
Figure 10:
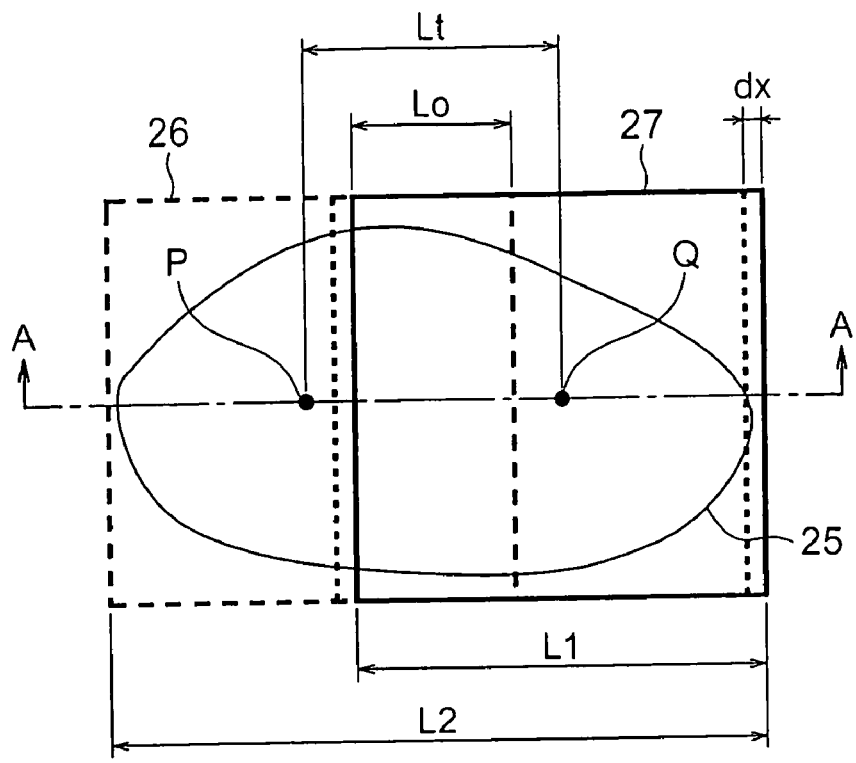
FIG. 10 is a plan view showing parameters of the irradiation field according to the first embodiment of the present invention.
Figure 11:
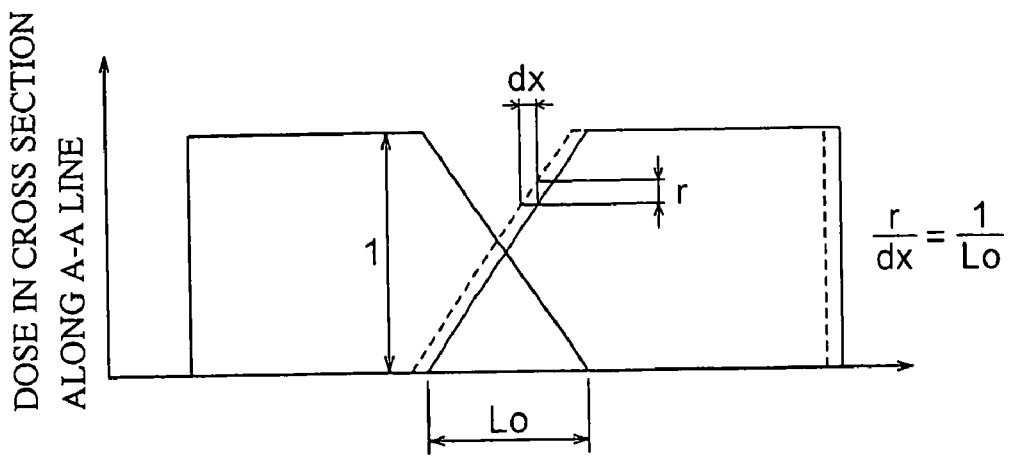
FIG. 11 is a dose distribution chart in cross section along line A—A of FIG. 10.

Now, reference will be made to the enlargement of the irradiation field by means of the irradiation apparatus according to the first embodiment of the present invention. FIG. 8 is a plan view that shows the irradiation field of the irradiation apparatus according to the first embodiment of the present invention. FIGS. 9A and 9B are dose distribution charts of the irradiation field in cross section along line A—A of FIG. 8, wherein FIG. 9A shows dose distributions in respective irradiation zones, and FIG. 9B shows a total dose distribution over the entire irradiation zones. FIG. 10 is a plan view that shows parameters of the irradiation field according to the first embodiment of the present invention. FIG. 11 is a dose distribution chart in cross section along line A—A of FIG. 10. Here, note that the following explanation will be made with an assumption that. the outside shape of the target to be irradiated coincides with that of the irradiation field, and hence the irradiation field will be mainly referred to below but it also indicates the irradiated target, too. In addition, one irradiation means the irradiation of a radiation beam performed to one irradiation zone. One irradiation includes a plurality of partial irradiations which are carried out in succession by successively changing the outer peripheral configuration of each irradiation zone by moving a part of the leaves 23, as will be described later.

The method of enlarging the irradiation field is carried out as follows. That is, a first irradiation zone and a second irradiation zone, partially overlapping with each other, are formed by the operation of the multileaf collimator controller 15. The target 25 to be irradiated is moved by the position controller 13 to a new position where a new irradiation zone is formed, partially overlapping with but different from the original location. The irradiation field is enlarged by irradiating a beam to the first irradiation zone and the second irradiation zone through the beam interrupter 12. Here, note that though in the following description, the multileaf collimator controller 15 will not be referred to upon explaining the movement of the leaves 23 of the multileaf collimator 14, it always controls the multileaf collimator 14. Similarly, though not explained explicitly, the irradiation of the radiation beam is controlled by the beam interrupter 12. Moreover, it is assumed in the following explanation that the configuration of each irradiation zone is a square. As shown in FIG. 8, the target 25 to be irradiated is covered by a first square-shaped irradiation zone 26 enclosed by a solid line and a second square-shaped irradiation zone 27 enclosed by a broken line. A portion or area, in which the first irradiation zone 26 and the second irradiation zone 27 overlap with each other, is called the overlapping zone 28, and those portions of the first and second irradiation zones 26, 27 which do not overlap with each other are called non-overlapping zones 29. In FIG. 8, the boundaries between the overlapping zone 28 and the non-overlapping zones 29 become straight lines, respectively, but they need not necessarily be straight lines and may be curved lines.

The maximum opening of the irradiation zone when the leaves 23 of the multileaf collimator 14 are opened to a maximum size is a square. The amount of dose of the overlapping zone 28 between the first and second irradiation zones 26, 27 decreases along a slope approximated by a straight line from the non-overlapping zones 29 toward the overlapping zone 28. Here, in order to make the explanation easy to understand, the decreasing slope of the dose is approximated by not a stepped line but a straight line. That is, the leaves 23 of the multileaf collimator 14 are not moved stepwise but continuously. Furthermore, irradiation is performed such that the total dose distribution of the overlapping zone 28 between the first and second irradiation zones 26, 27 is flat, and the total amount of dose thereof becomes equal to the dose of the non-overlapping zones 29.

Next, reference will be made to a method of obtaining the width of the overlapping zone 28 between the first and second irradiation zones 26, 27 partially overlapping with each other as well as a method of obtaining the step width of movement of the leaves 23. To ensure a wide irradiation field, the overlapping zone 28 should be decreased as much as possible, however, it is necessary to increase the overlapping zone 28 to a sufficient extent so as to decrease the error in the flatness of the dose distribution due to positioning errors below a predetermined value. As shown in FIG. 10, a symbol L1 designates the width of a maximum opening in the direction of the X axis when the leaves 23 of the multileaf collimator 14 are opened to a maximum, and L2 designates the width of a maximum irradiation field in the direction of the X axis when the two irradiation zones 26, 27 come to partially overlap with each other. The width Lo of the overlapping zone 28 in the X axis direction is given by the following expression (1) based on a positioning error dx and a flatness error r for the required flatness.

$$Lo = dx/r \tag{1}$$

Further, the moving distance Lt of the irradiation table 7 is given by an equation in the form of Lt=L1−Lo.

In addition, the width L2 of the maximum irradiation field has a certain relation established between the positioning error dx and the width Lo of the overlapping zone 28 in the direction of the X axis, as represented by the following expression (2).

$$L2 = 2 \times L1 - Lo = 2 \times L1 - dx/r \tag{2}$$

By using expression (2) above, the relation between the positioning error dx, the maximum irradiation field L2 and the width Lo of the overlapping zone as required are represented by the following Table 1 with assumptions of L1=150 mm and r=2.5%.

Table 1

Relations Between the Positioning Error and the Other Parameters

| Positioning error dx mm | Maximum irradiation range L2 mm | Overlap between irradiation zones Lo mm | Moving distance of irradiation table Lt mm |
|---|---|---|---|
| 0.5 | 290 | 10 | 140 |
| 1 | 280 | 20 | 130 |
| 1.5 | 270 | 30 | 120 |
| 2 | 260 | 40 | 110 |
| 2.5 | 250 | 50 | 100 |
| 3 | 240 | 60 | 90 |
| 3.5 | 230 | 70 | 80 |
| 4 | 220 | 80 | 70 |
| 4.5 | 210 | 90 | 60 |
| 5 | 200 | 100 | 50 |

For instance, when the positioning error dx is 3 mm, the required width Lo of the overlapping zone becomes 60 mm and the width L2 of the maximum irradiation field is obtained to be 240 mm.

Then, a method of obtaining the step width of movement of the leaves 23 will be described. Though the positions of the leaves 23 have been explained as being made continuously variable in the foregoing description, reference will hereinafter be made to the positions of the leaves 23 being controlled in a stepwise manner. In order to keep the flatness error r of the dose distribution equal to or below a predetermined value, it is necessary to set the maximum step width s of the movement of the leaves 23 to a prescribed value of Lo×r. Additionally, as already stated, when considering multiple scattering which contributes to leveling the dose distribution, the error r in the dose flatness decreases.

Figure 12:
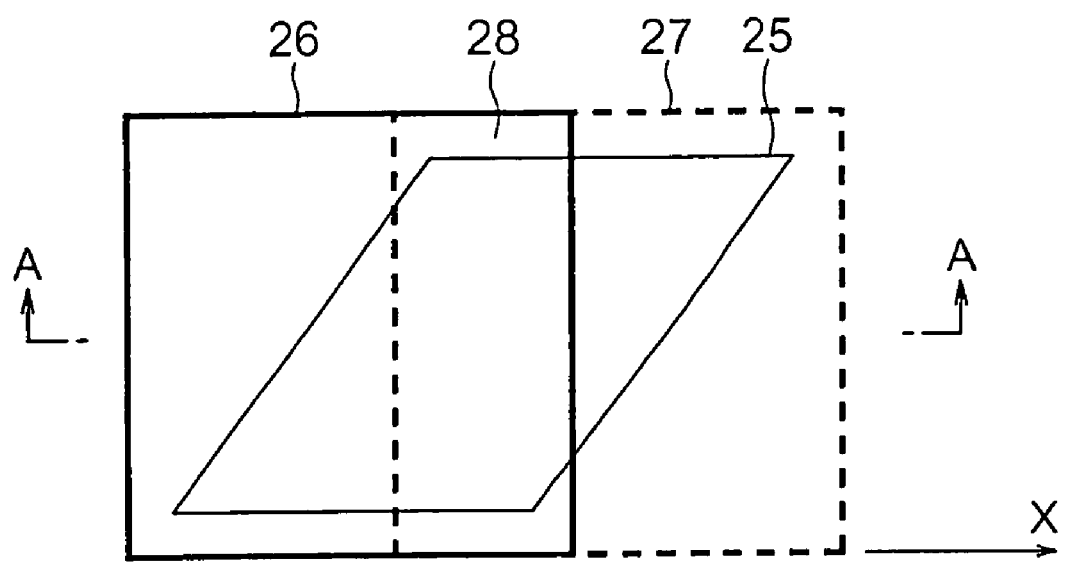
FIG. 12 is a conceptual diagram explaining the movement of leaves of the multileaf collimator in the first embodiment of the present invention.
Figure 13:
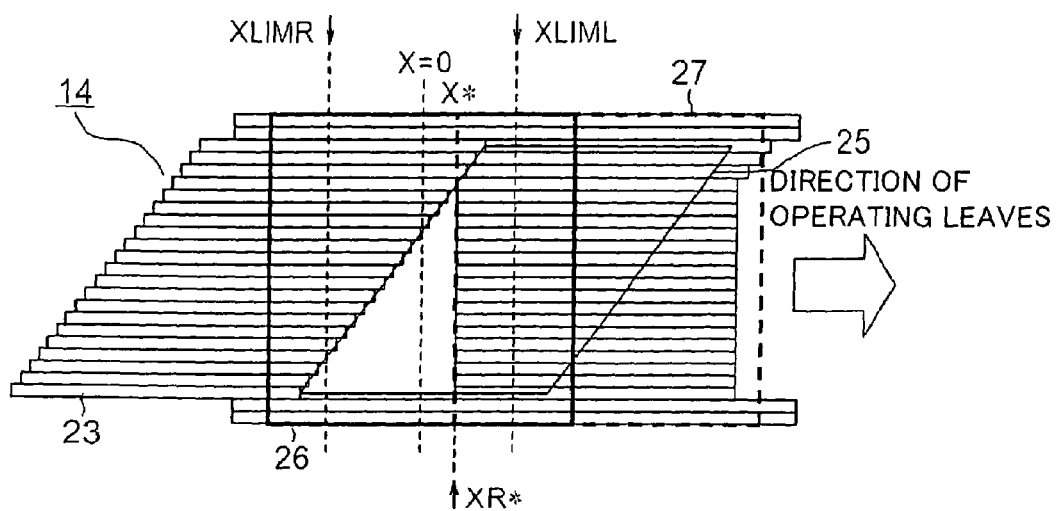
FIG. 13 is a plan view explaining the movement of the leaves of the multileaf collimator corresponding to a first irradiation zone in FIG. 12.
Figure 14:
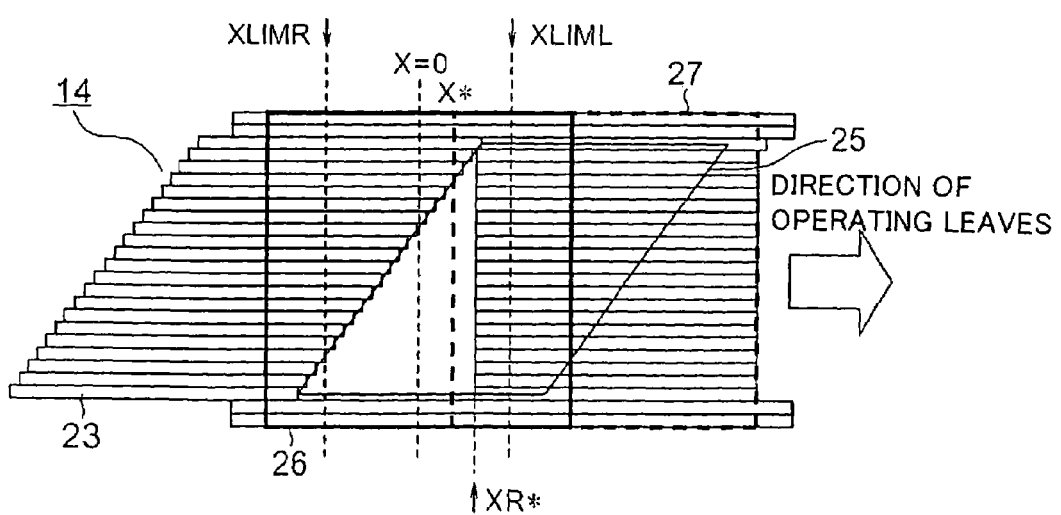
FIG. 14 is a plan view showing the leaves of FIG. 13 in the course of its movement.
Figure 15:
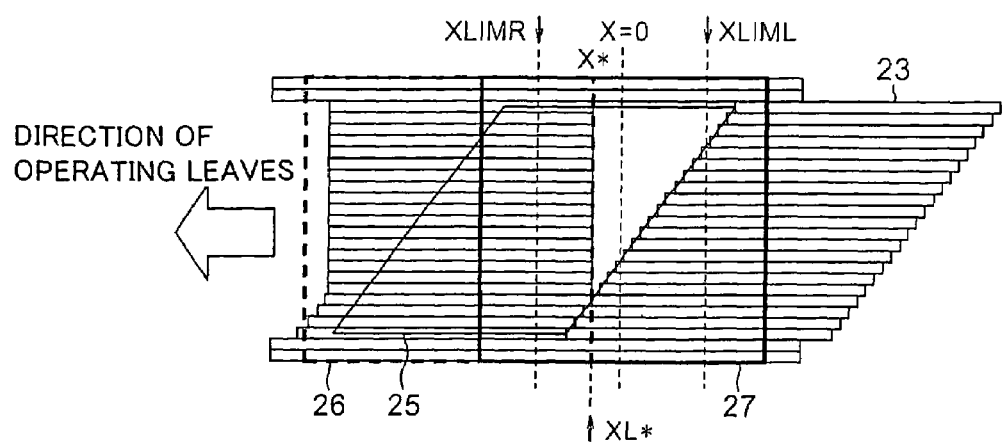
FIG. 15 is a plan view explaining the movement of the leaves of the multileaf collimator corresponding to a second irradiation zone in FIG. 12.
Figure 16:
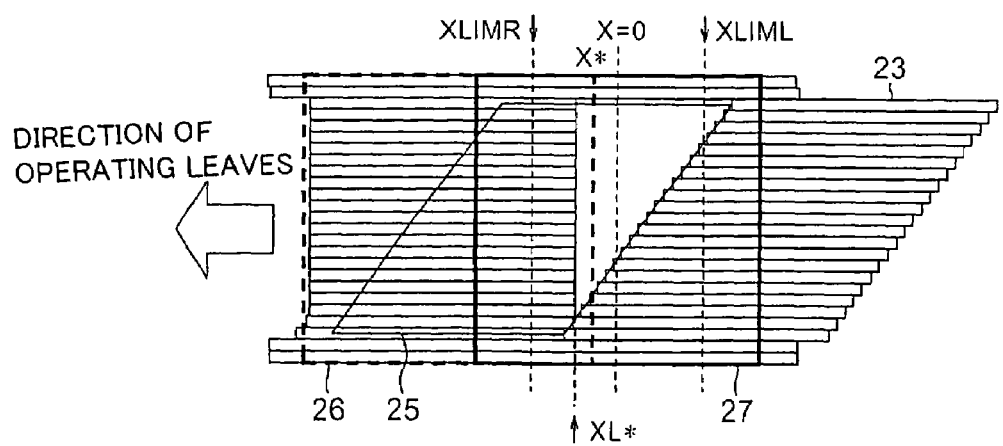
FIG. 16 is a plan view showing the leaves of FIG. 15 in the course of its movement.

Next, reference will be made to the operational steps of the leaves to obtain the above-mentioned dose distribution. FIG. 12 is a conceptual diagram that explains the movement of the leaves 23 of the multileaf collimator 14 in the first embodiment. FIG. 13 is a plan view that explains the movement of the leaves 23 of the multileaf collimator 14 corresponding to the first irradiation zone in FIG. 12. FIG. 14 is a plan view that shows the state of the leaves 23 in FIG. 13 during movement thereof. FIG. 15 is a plan view that explains the movement of the leaves 23 of the multileaf collimator 14 corresponding to the second irradiation zone in FIG. 12. FIG. 16 is a plan view that shows the of the leaves 23 in FIG. 15 during movement thereof. Although for the sake of easy understanding in the following explanation, it is assumed that the configuration of the location to be irradiated is a parallelogram and that the direction of movement of the leaves 23 is along the X axis, the location to be irradiated may take another configuration.

First of all, the dimensions (i.e., vertical and horizontal lengths) of the target 25 to be irradiated are measured, and the width Lo of the overlapping zone 28 and the step width s are determined according to Table 1 above by using the positioning error dx and the flatness error r measured in advance, as described above. Then, the first irradiation zone 26 and the second irradiation zone 27 are set along the major or longitudinal axis of the target 25 to be irradiated. The first irradiation zone 26 is first irradiated and the second irradiation zone 27 is then irradiated with the direction of movement of the leaves 23 of the multileaf collimator 14 being set in parallel with the slope of the dose.

FIG. 13 is a plan view that shows the positions of the leaves 23 when the irradiation to the first irradiation zone 26 is started. It is assumed that the center of the width L1 of the maximum opening of the leaves 23 of the multileaf collimator 14 enclosed by the thick solid line on the X axis is X=0, and that the x coordinate of the end face of each of the leaves 23 is defined at the widthwise center thereof with the x coordinates of the end faces of i-th left-hand and i-th right-hand ones of the leaves 23 being represented by XL(i) and XR(i), respectively. It is also assumed that the x coordinate of the left-hand end face of the overlapping zone 28 is X*. An override is provided to the leaves 23 so that the right-hand and left-hand leaves can move to the left or right beyond X=0. In addition, it is further assumed that the rightward operation limit of the left-hand leaves is represented by XLIML and the leftward operation limit of the right-hand leaves is represented by XLIMR, and that the x coordinates of the left-hand end face and the right-hand end face of the location to be irradiated in each leaf are represented by XTARL(i) and XTARR(i), respectively. It is also assumed that the x coordinates of the right-hand end face and the left-hand end face of each of those left-hand and right-hand leaves which do not lie in the location to be irradiated are 0. When the first irradiation zone 26 is irradiated, most of the right-hand leaves perform the same operation except for a part thereof, so the x coordinates XR(i) of the left-hand end faces of the right-hand leaves can be placed with a common coordinate XR*, whereas when the second irradiation zone 27 is irradiated, the left-hand leaves can be similarly defined with a common coordinate XL*.

The initialization of the leaf position in the first irradiation zone 26 is given by the following expressions (3) through (6). Here, it is assumed that the x axis in FIG. 13 is positive to the right from the origin, and negative to the left from the origin.

$$XL(i) = \min(XTARL(i), XLIML) \quad (3)$$

$$XR^* = X^* \quad (4)$$

$$R(i) = \max(XR^*, XL(i)) \quad (5)$$

$$XR(i) = \min(XR(i), XTARR(i)) \quad (6)$$

Under the above conditions, when it is detected by the dose monitor 11 that a fixed dose has been irradiated, the beam is stopped. This state is called "partial dose completion". Then, the "partial dose completion" is reset, and the position of the right-hand leaves is moved stepwise to the right by a step width s, as indicated by the following expressions (7) through (9), so that irradiation is carried out until the "partial dose completion" is reached.

$$XR^* = XR^* + s \quad (7)$$

$$XR(i) = \max(XR^*, XL(i)) \quad (8)$$

$$XR(i) = \min(XR(i), XTARR(i)) \quad (9)$$

The state in which the leaves 23 have been moved halfway to the right is shown in FIG. 14. By repeatedly moving the leaves 23 stepwise to the right by the step width s in this manner, those of the right-hand leaves 23 of which left-hand end faces have reached the right-hand end face of the target 25 to be irradiated are stopped in their rightward movement, and when the XR* has reached the right-hand end face of the first irradiation zone 26, the irradiation of the first irradiation zone 26 is ended.

Subsequently, the irradiation table 7 is moved by a prescribed distance Lt, and the second irradiation zone 27 is irradiated. The procedure for this case is that the operation of the first irradiation zone 26 is carried out symmetrically with respect to the x axis. That is, the leaf positions are initialized according to the following expressions (10) through (13). The initial settings of the leaves 23 are shown in FIG. 15.

$$XR(i) = \max(XTARR(i), XLIMR) \quad (10)$$

$$XL^* = X^* \quad (11)$$

$$XL(i) = \min(XL^*, XR(i)) \quad (12)$$

$$XL(i) = \max(XL(i), XTARL(i)) \quad (13)$$

Irradiation is carried out until the "partial dose completion" is obtained, whereafter the beam is stopped and the positions XL(i) of the left-hand leaves 23 are moved stepwise to the left by the step width s according to the following expressions (14) through (16).

$$XL^* = XL^* - s \quad (14)$$

$$XL(i) = \min(XL^*, XR(i)) \quad (15)$$

$$XL(i) = \max(XL(i), XTARL(i)) \quad (16)$$

The state in which the leaves 23 have been moved halfway to the left is shown in FIG. 16. By repeatedly moving the leaves 23 stepwise to the left by the step width s in this manner, those of the left-hand leaves 23 of which right-hand end face reaches the left-hand end face of the target 25 to be irradiated are stopped in their leftward movement, and when the XL* has reached the left-hand end face of the second irradiation zone 27, the irradiation of the second irradiation zone 27 is ended, thus completing the entire irradiation.

Figure 17A:
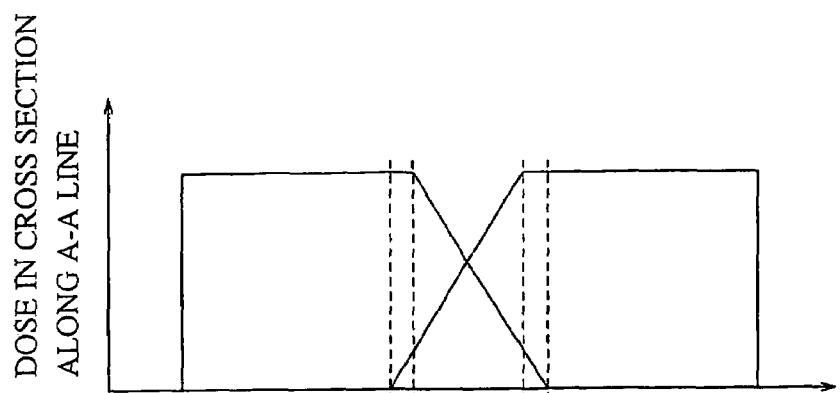
FIGS. 17A and 17B are individual and total dose distribution charts, respectively, in the case where two irradiation zones are too near to each other in the first embodiment of the present invention.
Figure 17B:
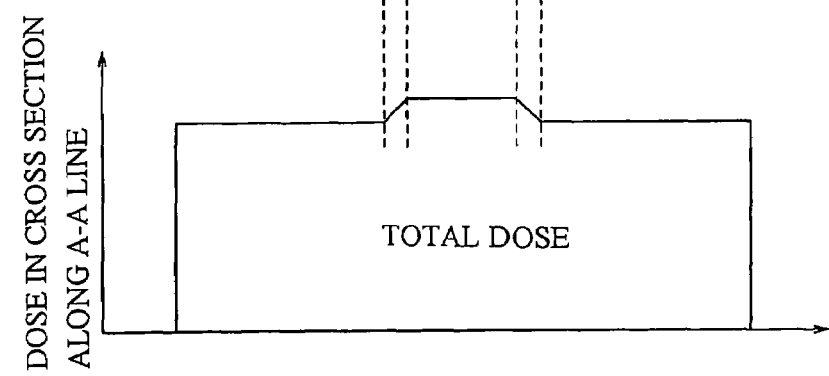
Figure 18A:
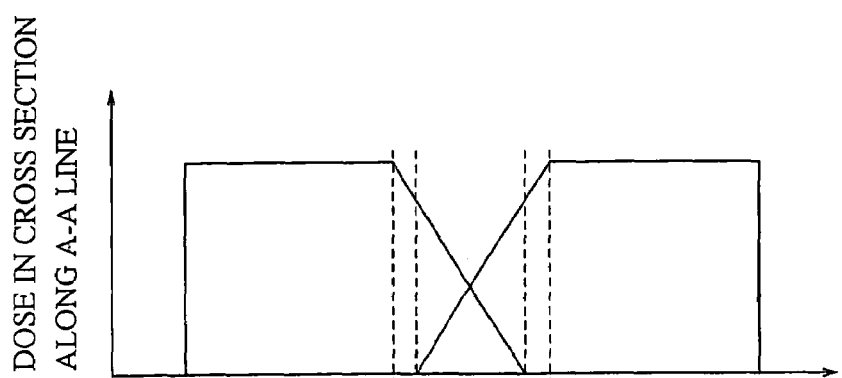
FIGS. 18A and 18B are individual and total dose distribution charts, respectively, in the case where two irradiation zones are too far away from each other in the first embodiment of the present invention.
Figure 18B:
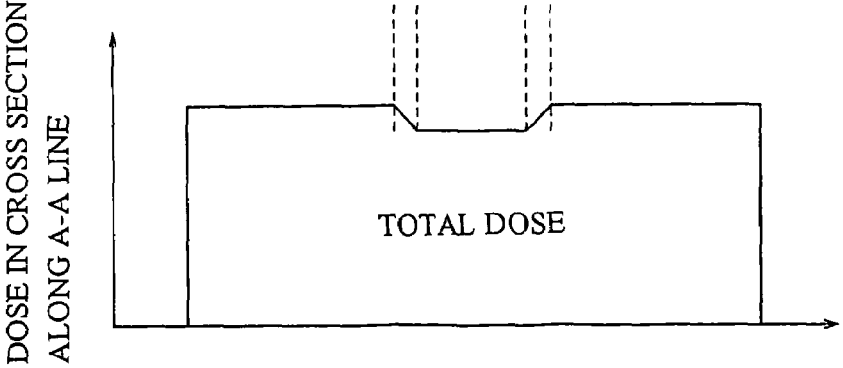
Figure 21A:
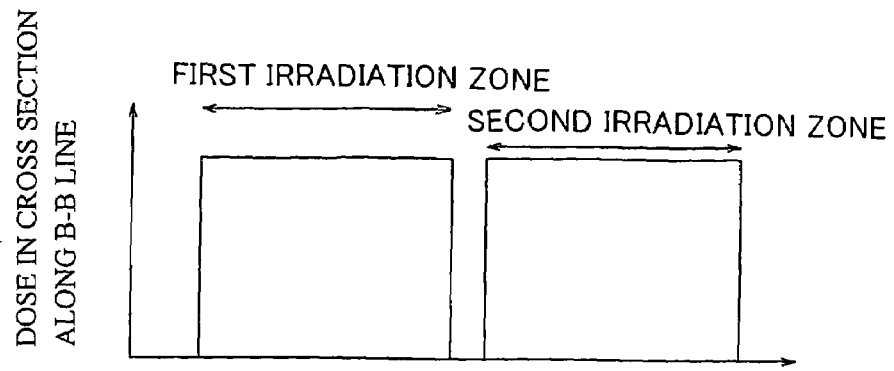
FIGS. 21A and 21B are individual and total dose distribution charts, respectively, in the case where the two irradiation zones are separated from each other.
Figure 21B:
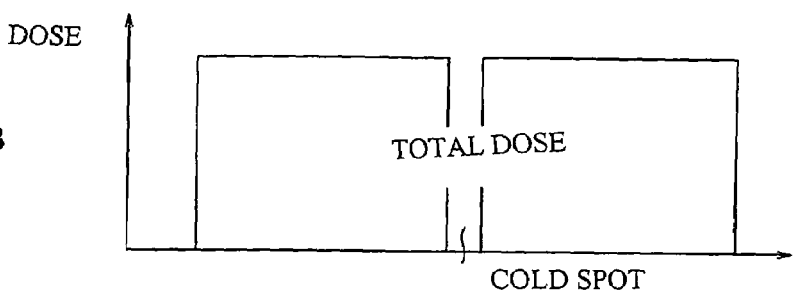
Figure 22A:
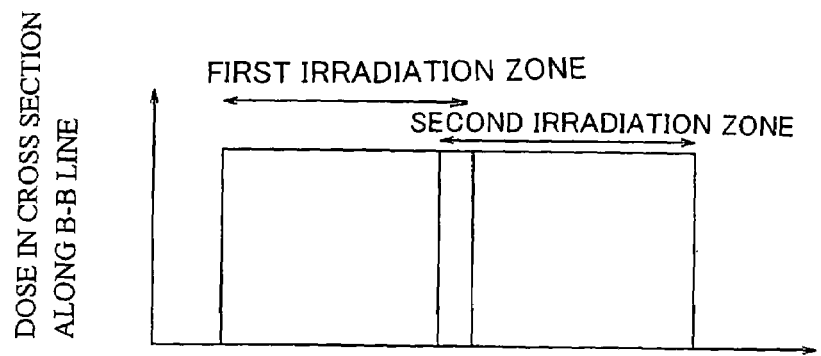
FIGS. 22A and 22B are individual and total dose distribution charts, respectively, when the two irradiation zones partially superpose with each other.
Figure 22B:
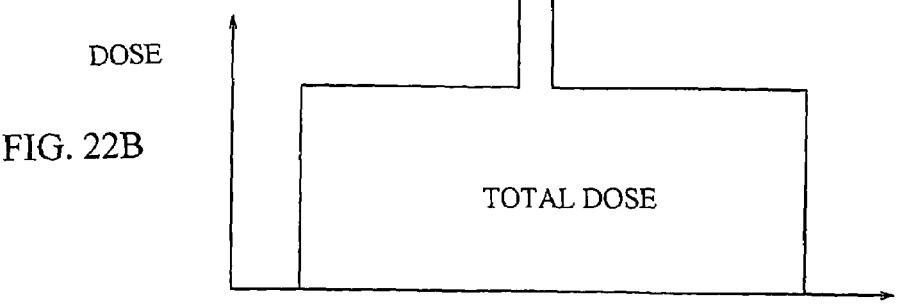

Now, reference will be made to the advantageous effects of the present invention. FIGS. 17A and 17B show individual and total dose distributions, respectively, in case where the two irradiation zones are disposed too near to each other in the first embodiment. FIGS. 18A and 18B show individual and total dose distributions, respectively, in case where the two irradiation zones are disposed too far from each other in the first embodiment. FIG. 19 is a plan view of an irradiation field having two irradiation zones 30, 31 without any overlapping zone, in which the dose distributions in the first irradiation zone 30 and the second irradiation zone 31 are flat over all the entire zones. FIGS. 20A and 20B show individual and total dose distributions, respectively, in cross section along line B—B when the two irradiation zones 30, 31 in FIG. 19 are in contact with each other at their boundary. FIGS. 21A and 21B are individual and total dose distributions, respectively, in cross section along line B—B when the two irradiation zones in FIG. 19 are separated from each other. FIGS. 22A and 22B are individual and total dose distributions, respectively, in cross section along line B—B when the two irradiation zones in FIG. 19 partially superpose with each other.

The relative positions of the first irradiation zone 26 and the second irradiation zone 27 might be shifted due to various factors. However, it is understood that, even in such a case, the variation of the total dose in the overlapping zone 28 can be limited according to the present invention. That is, even if the two irradiation zones are disposed too near with respect to each other, the flatness of the total dose still remains within tolerance, as shown in FIGS. 17A and 17B. Also, even if the two irradiation zones are disposed too far away from each other due to a deviation in the positioning thereof, the flatness of the total dose similarly remains within tolerance, as shown in FIGS. 18A and 18B.

In contrast to this, when patch field irradiations are carried out simply as shown in FIG. 19, there will take place an overlapping area or a separated area due to a positioning deviation or shift, thus resulting in an insufficient degree of flatness of the dose distribution. If the two irradiation zones are too far away from each other, there will take place a cold spot, as shown in FIGS. 21A and 21B, whereas if the two zones are too near to each other, there will take place a hot spot, as shown in FIGS. 22A and 22B. In both of these cases, the total dose varies in the range of +/−100% with respect to a desired dose, which greatly exceeds a normal tolerance range of +/−2.5%.

In the above explanation about the advantageous effects; no consideration has been given to the effect of scattering. Accordingly, reference will hereinafter be made to the advantageous effects of the present invention by using rough values while taking account of the scattering effect. Here, note, however, that the scattering effect is less in the vicinity of the patient's body surface, so the discussion thus far is generally applicable to the dose distribution in the vicinity of the body surface. In the deep interior of the body, the divergence or spread of the beam due to multiple scattering can be approximated by a Gaussian distribution with a standard deviation $\sigma$. The maximum range of a proton beam with an energy of 250 MeV is about 37 cm in water, and scattering becomes a Gaussian distribution with a standard distribution $\sigma$ of about 8 mm. In FIGS. 22A and 22B, assuming that the position error of overlapping is 3 mm and an excess dose at the hot spot is 100 units/mm for instance, an integrated amount of the excess dose becomes about 300 units.

Given a Gaussian distribution for scattering of the above condition, it can be represented by the following expression (17), which is standardized to keep the integrated excess dose of 300 units.

$$f(x)=300/[\text{sqrt}(2\pi)\ \sigma]\ \exp(-x^2/2\sigma^2) \tag{17}$$

Also, in case of $\sigma=8$ mm, it can be represented by the following expression (18).

$$f(x)=15.0\ \exp(-x^2/2\sigma^2) \tag{18}$$

In other words, at $x=0$, the excess dose will be made flat up to about 15 units/mm. However, it is understood that with such simple overlapping, the nonuniformity of the dose due to the positioning error is large even when the excess dose is maximally flattened by the multiple scattering.

Since this irradiation apparatus is able to create a slope gradient of the dose in the overlapping portion of the two irradiation zones, the irradiation field can be enlarged and the flatness of the dose distribution can be improved easily.

In addition, since the dose slope can be approximated by a straight line, the operation or manipulation of the leaves corresponding to the overlapping zone of each of the irradiation zones can be facilitated. Moreover, since the dose slope is parallel to the moving direction of the leaves, it is possible to achieve a straight slope by pulling out the leaves at a constant speed.

Further, since the leaves can be driven in a stepwise manner, it is possible to simplify the construction of the drive unit for driving the leaves.

Furthermore, the irradiation field can be nearly shaped into the configuration of the location to be irradiated by changing the moving pattern of the leaves, whereby the irradiation apparatus becomes able to have a greater degree of freedom.

Still further, the influence of radiation on the operators and technologists can be reduced by manipulating the multileaf collimator through remote control.

Besides, the radiotherapy apparatus provided with such irradiation apparatuses is able to treat a large target or area, an elongated target or area, etc.

Here, note that although one example has been described in which the slope of the dose distribution is approximated by a straight line, it is similarly possible to enlarge the irradiation field even if approximated by a curved line.

Embodiment 2.

Figure 23A:
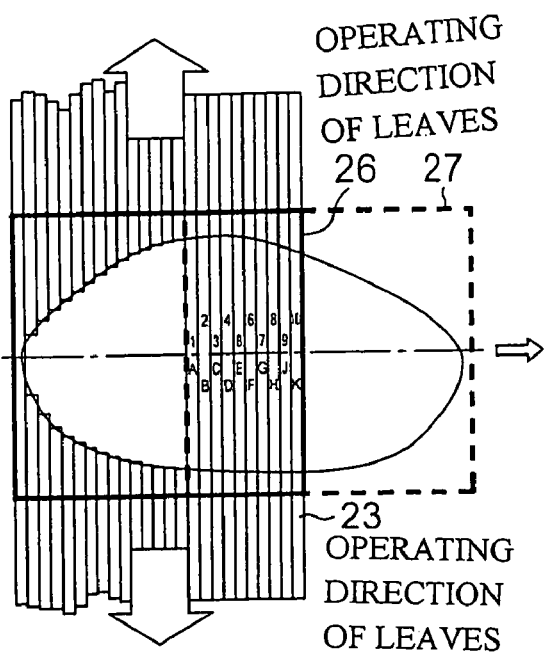
FIGS. 23A through 23D are plan views explaining the movement of leaves of a multileaf collimator in an irradiation apparatus according to the second embodiment of the present invention.
Figure 23B:
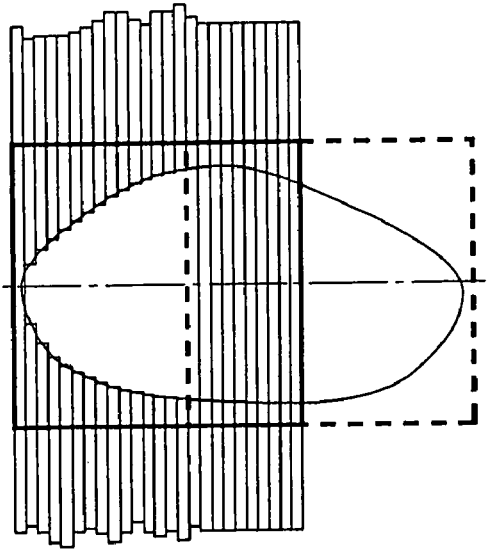
Figure 23C:
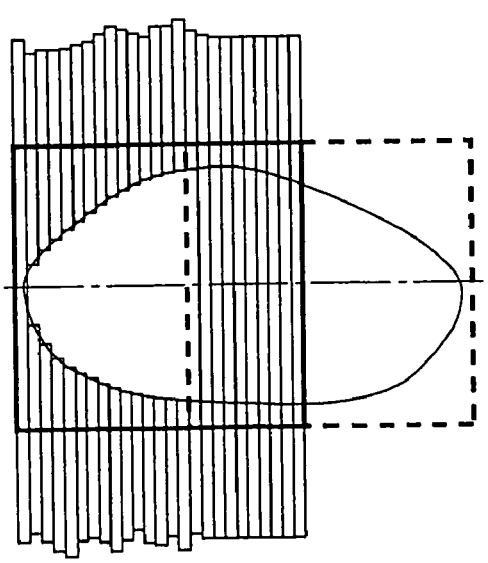
Figure 23D:
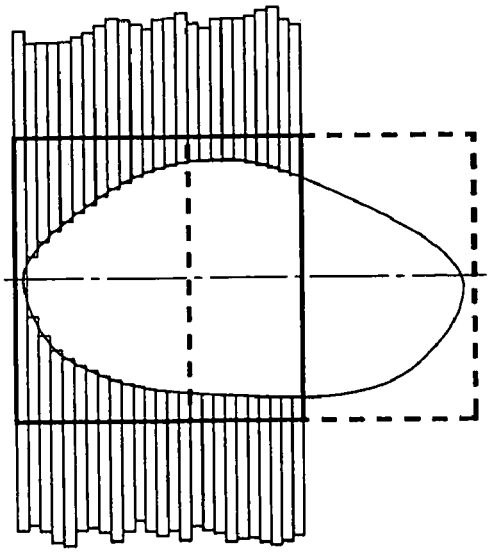

FIGS. 23A through 23D are plan views explaining the movement of the leaves of a multileaf collimator in an irradiation apparatus according to a second embodiment of the present invention, wherein FIG. 23A shows the initial positions of the leaves in which they are all closed; FIG. 23B shows that a first pair of leaves are opened with the remaining leaves being closed; FIG. 23C shows that a second pair of leaves are subsequently opened with the remaining leaves other than the first and second pairs being closed; and FIG. 23D shows that the last pair of leaves are finally opened.

In the first embodiment, the direction in which the leaves are driven to move is parallel to the slope of the dose distribution, but this second embodiment is constructed such that the moving direction of the leaves is perpendicular to the slope of the dose distribution. In this case, each time a predetermined amount of dose is irradiated with partial irradiation, i.e., each time the irradiation of a partial dose is completed, the leaves 23 covering the overlapping zone are opened sequentially in the order from the leaves of the greatest dose requirement to the leaves of the least dose requirement. Specifically, in FIGS. 23A through 23D, the leaves 23 are opened sequentially from a pair of leaf 1 and leaf A. After the irradiation of the first irradiation zone 26 is finished in this manner, the irradiation table 7 is moved to a prescribed position where the second irradiation zone 27 is irradiated according to a symmetrical or similar procedure. In this second embodiment, a minimum step of the slope of the dose distribution is decided depending on a leaf width (i.e., the width of each leaf), it is necessary to determine the width of the overlapping zone in consideration of the leaf width s, as shown in Table 1.

Such an irradiation apparatus can adjust the slope of the dose distribution of the overlapping zone by a step width comprising the leaf width, and hence such an adjustment can be made merely by pulling put the leaves and hence is not subjected to the influence of the positioning accuracy of the leaves. Thus, an error in the flatness of the dose distribution is decided by the leaf width alone, thereby making it possible to enhance the accuracy of the dose distribution flatness. Further, since the slope of the dose distribution is perpendicular to the moving direction of the leaves, the positional adjustment of the plurality of irradiation zones can be achieved only by adjusting the leaf positions.

Embodiment 3.

Figure 24A:
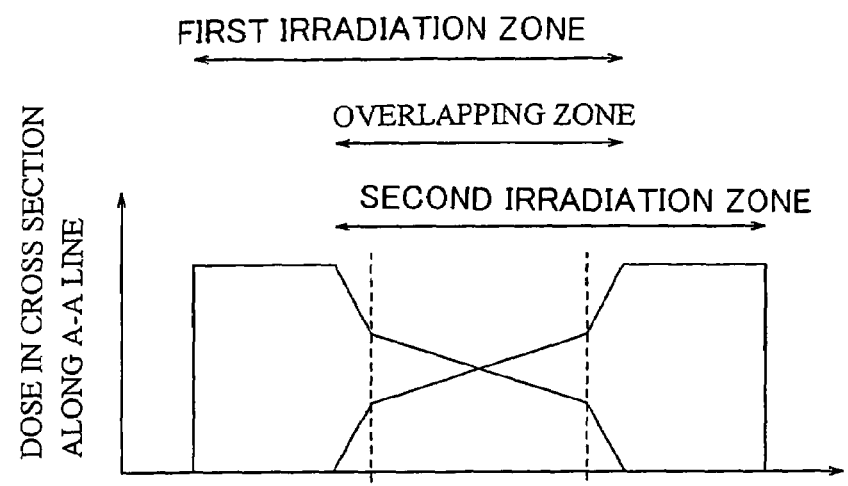
FIGS. 24A and 24B are individual and total dose distribution charts, respectively, when an irradiation apparatus according to the third embodiment of the present invention is used.
Figure 24B:
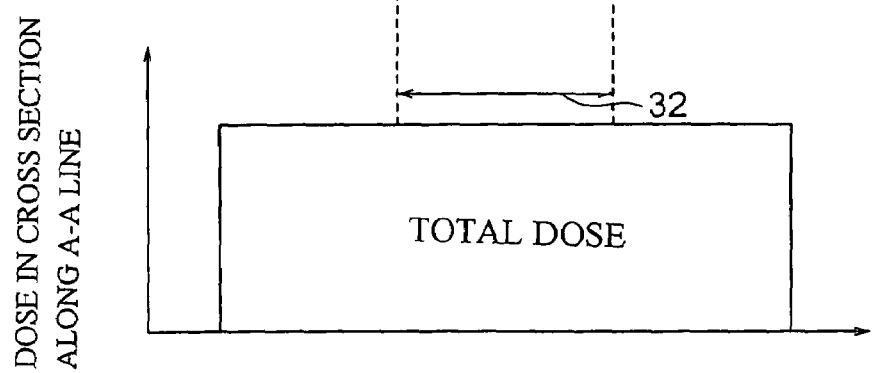

FIGS. 24A and 24B show individual and total dose distributions, respectively, when an irradiation apparatus according to a third embodiment of the present invention is used.

In the above-mentioned first embodiment, the dose in the overlapping zone has been decreased at a constant slope from the non-overlapping zone toward its adjoining irradiation zones, but according to this third embodiment, in order to reduce the flatness in the dose distribution in an important area 32 in which the dose distribution flatness is particularly critical, the slope of the dose distribution in the important area 32 is made gradual, with the dose distribution slope in the other portions of the overlapping zone being made steep in comparison with that in the important area 32, as shown in FIGS. 23A through 23D.

This irradiation apparatus is able to make the overlapping error of the dose in the overlapping zone smaller for concentrated administration thereof.

Although in the foregoing description, the dose distribution changes according to a slope approximated by a straight line, similar advantageous effects will be obtained even if the dose distribution changes according to a slope approximated by a polygonal line, a curved line, etc., other than a straight line.

Embodiment 4.

Figure 25:
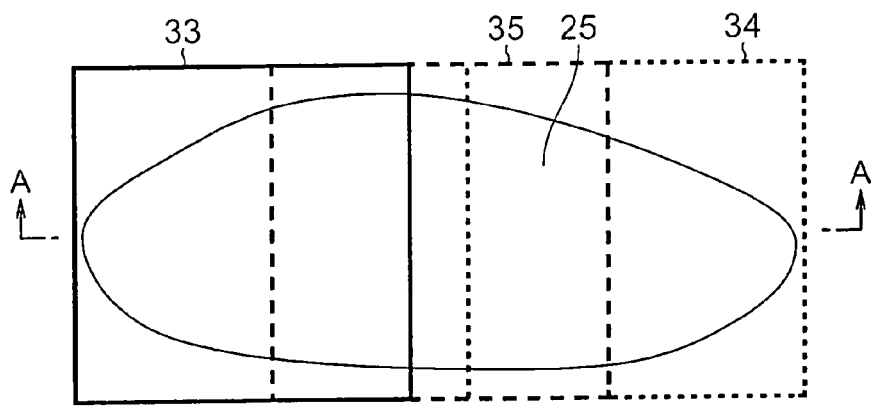
FIG. 25 is a plan view of an irradiation field when an irradiation apparatus according to the fourth embodiment of the present invention is used.
Figure 26:
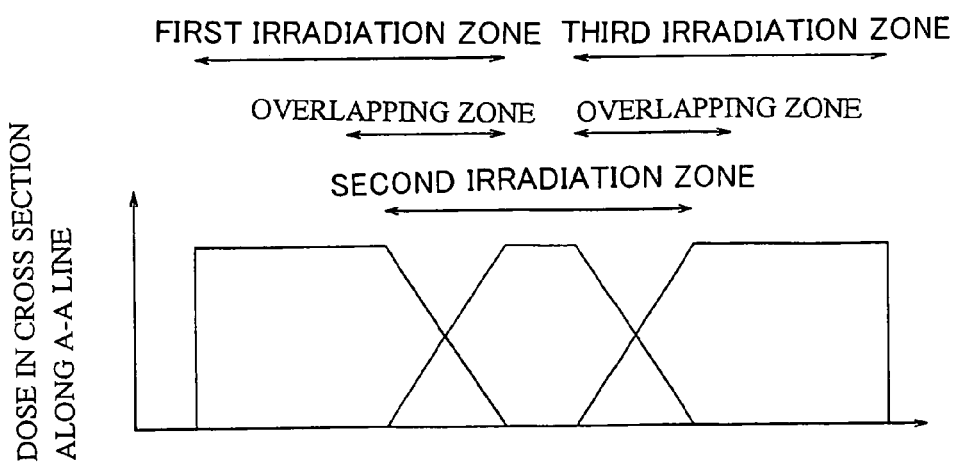
FIG. 26 is a dose distribution chart in cross section along line A—A of FIG. 25.
Figure 27:
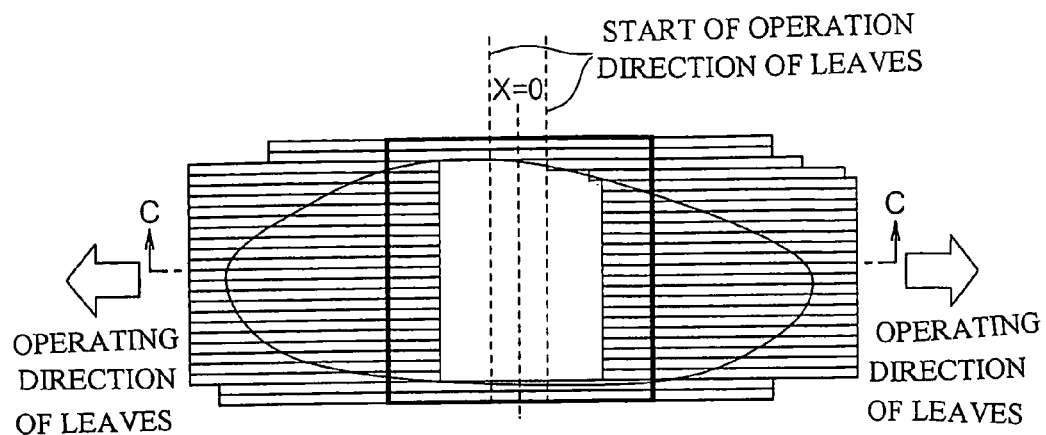
FIG. 27 is a plan view showing the movement of leaves of a multileaf collimator parallel to a dose slope in the irradiation apparatus according to the fourth embodiment of the present invention.
Figure 28:
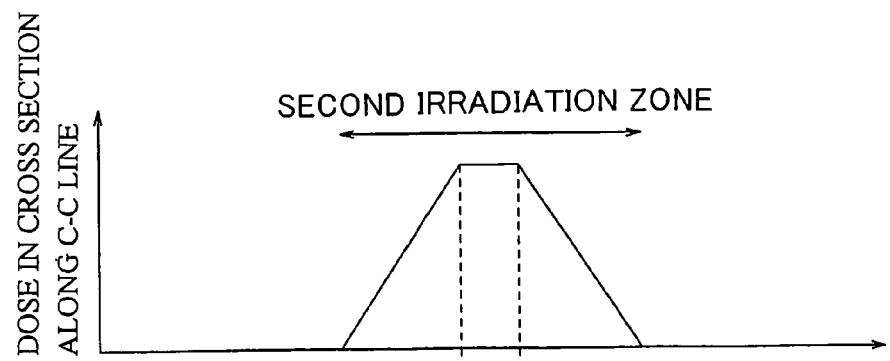
FIG. 28 is a dose distribution chart in cross section along line C—C of FIG. 27.
Figure 29:
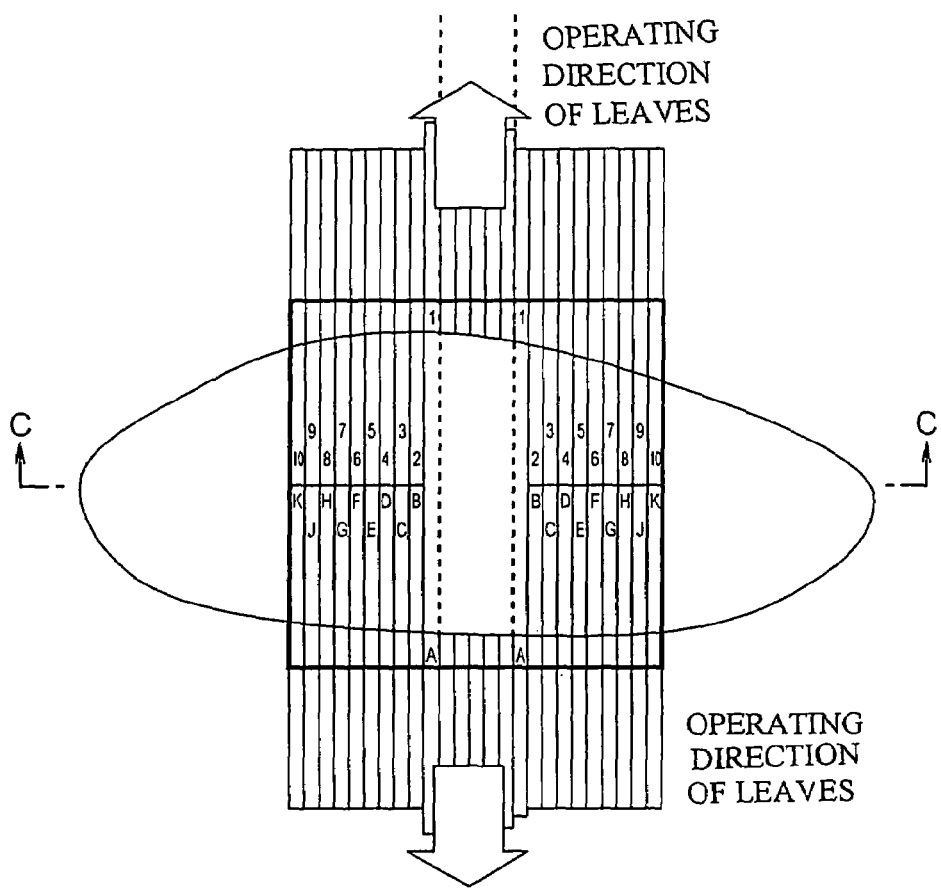
FIG. 29 is a plan view showing the movement of the leaves of the multileaf collimator perpendicular to the dose slope in the irradiation apparatus according to the fourth embodiment of the present invention.
Figure 30:
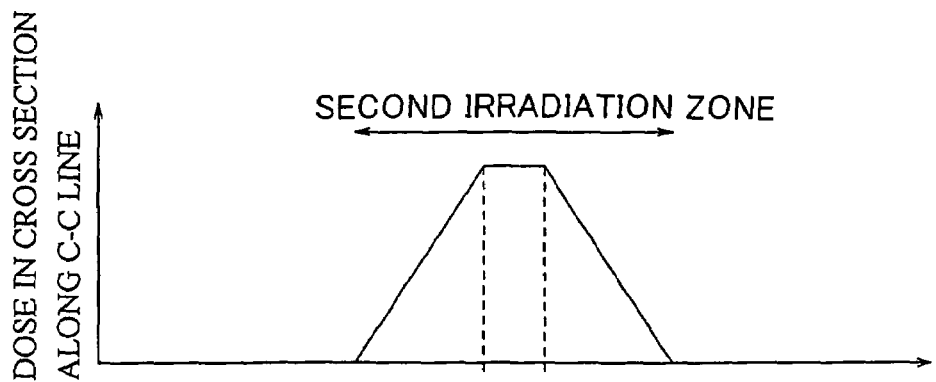
FIG. 30 is a dose distribution chart in cross section along line C—C of FIG. 29.
Figure 31:
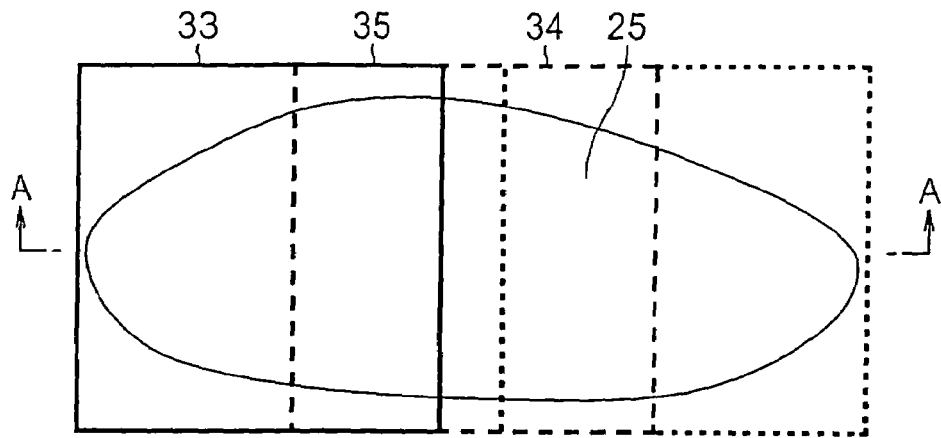
FIG. 31 is a plan view of an irradiation field when an irradiation apparatus according to a fourth embodiment of the present invention is used.
Figure 32:
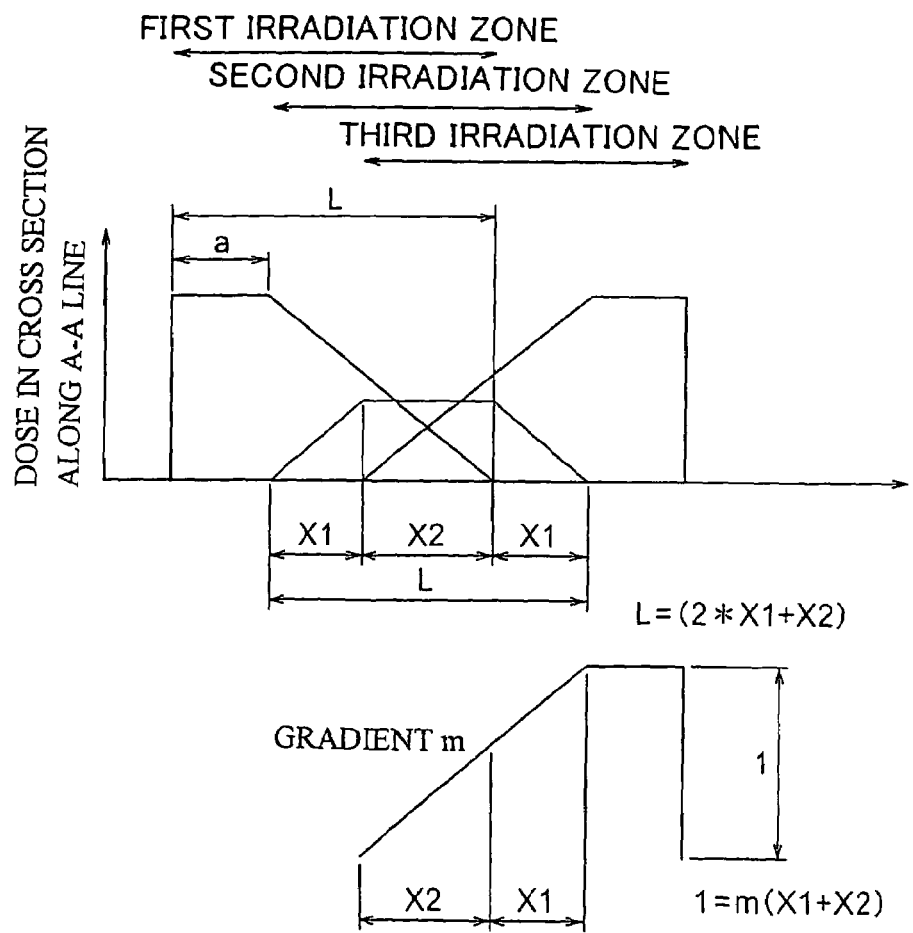
FIG. 32 is a dose distribution chart in cross section along line A—A of FIG. 31.

FIG. 25 is a plan view of an irradiation field when an irradiation apparatus according to a fourth embodiment of the present invention is used. FIG. 26 is a dose distribution chart of this irradiation field. FIG. 27 is a plan view that shows the movement, parallel to the dose slope, of leaves of a multileaf collimator in the irradiation apparatus according to the fourth embodiment of the present invention. FIG. 28 is a dose distribution chart of an irradiation zone irradiated in FIG. 27. FIG. 29 is a plan view that shows the movement, perpendicular to the dose slope, of the leaves of the multileaf collimator in the irradiation apparatus according to the fourth embodiment of the present invention. FIG. 30 is a dose distribution chart of an irradiation zone irradiated in FIG. 29. FIG. 31 is a plan view of an irradiation field when the irradiation apparatus according to the fourth embodiment of the present invention is used. FIG. 32 is a dose distribution chart of the irradiation field in FIG. 31.

In this fourth embodiment, three irradiation zones are employed in combination to further expand or enlarge the irradiation field, as shown in FIG. 25. In this case, a first irradiation zone 33 and a third irradiation zone 34 are similar to the first and second irradiation zones in the first embodiment, but a second irradiation zone 35 exhibits a triangular dose distribution. Irradiations to the first irradiation zone 33 and the third irradiation zone 34 can be made by moving the leaves in a manner similar to that of the above-mentioned first or second embodiment so that dose distributions in the overlapping zones of the first and third irradiation zones 33, 34 can be properly sloped. Then, reference will be made to the operation of the leaves with respect to the second irradiation zone 35 when the leaves are caused to move in a direction parallel to the dose slope, while referring to FIG. 27. The initial positions of the leaves are set to the boundaries of a flat area of the central portion, and the leaves are successively moved to open each time the irradiation of a partial dose has been completed. In addition, FIG. 29 shows the procedure in the operation of the leaves in case where the leaves are driven to move in a direction perpendicular to the dose slope. As shown in this figure, leaves 1 through 10 at one side and leaves A through K at the other side are sequentially moved to open in a pair of corresponding leaves at opposite sides each time the irradiation of a partial dose has been expired.

Moreover, when the slopes of the overlapping zones in FIG. 27 are made more gradual, the overlapping zones become further larger, as shown in FIG. 31. When the overlapping zones come to occupy more than a half of the maximum opening of the multileaf collimator, the three irradiation zones 33, 34 and 35 overlap with one another in an area of X2. Here, as shown in FIG. 32, let us assume that a symbol m represents the gradient of each dose slope portion in the second irradiation zone 35; L represents the width of the maximum opening of the multileaf collimator; X1 represents the width of each dose slope portion in the second irradiation zone 35; and X2 represents the width of a dose constant portion in the second irradiation zone 35. For the purpose of irradiating the greatest area, the widths of the first, second and third irradiation zones are set to L, respectively. In this case, the relations of these parameters are represented by the following expressions (19) and (20):

$$L=(2*X1+X2) \tag{19}$$

$$M(X1+X2)=1 \tag{20}$$

X1 and X2 are given by the following expressions (21) and (22) from expressions (19) and (20) above.

$$X1=(L-1)/m \tag{21}$$

$$X2=2/(m-L) \tag{22}$$

Such an irradiation apparatus provides a wider irradiation field than the case where only two irradiation zones are overlapped with each other.

Further, by making the slopes of the overlapping zones more gradual, the overlapping zones can be further increased, thereby further improving the flatness of the total dose distribution.

Embodiment 5.

Figure 33:
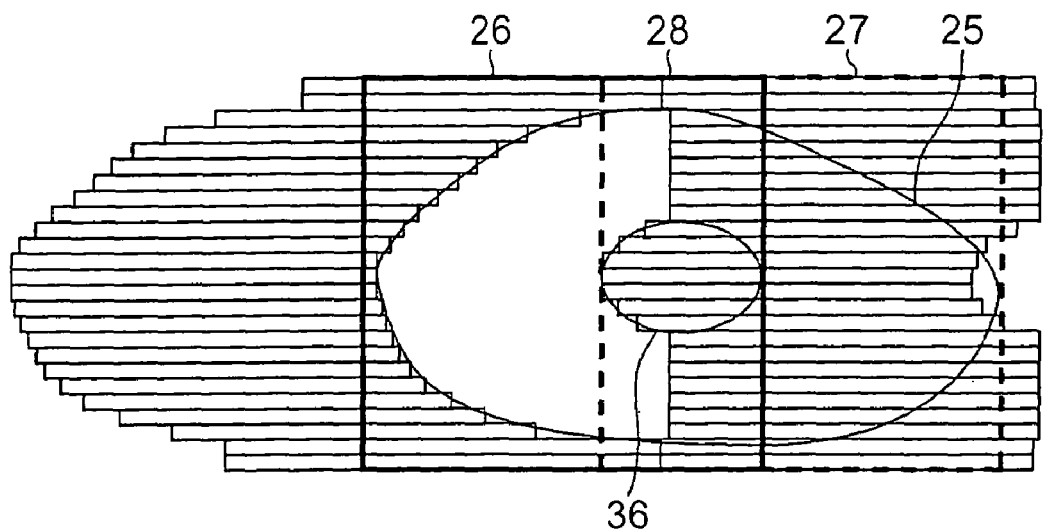
FIG. 33 is a plan view showing the movement of leaves of a multileaf collimator in an irradiation apparatus according to a fifth embodiment of the present invention.
Figure 34:
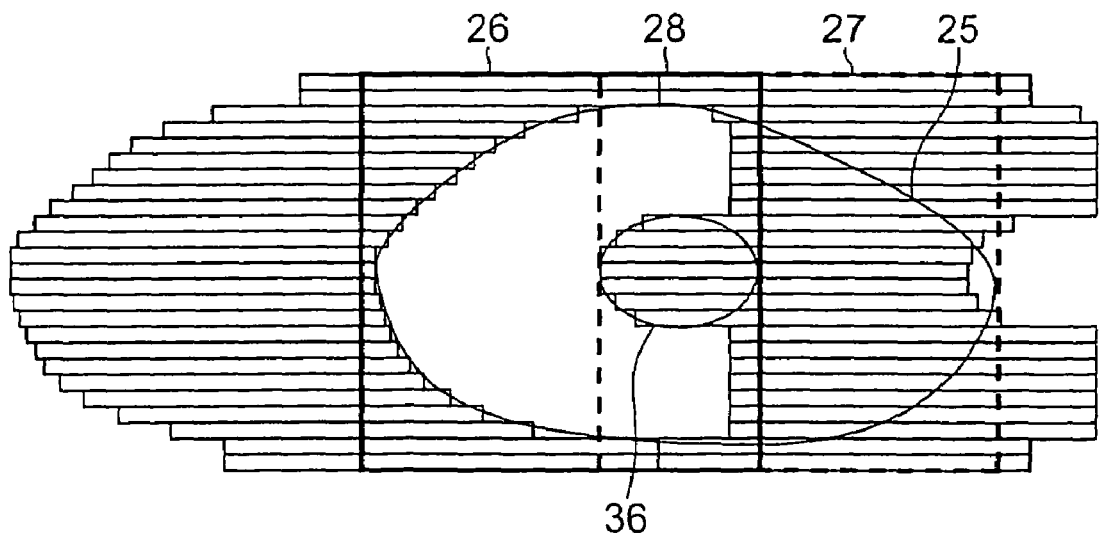
FIG. 34 is a plan view showing the leaves of FIG. 33 in the course of its movement.

FIG. 33 is a plan view that shows the movement of leaves of a multileaf collimator in an irradiation apparatus according to the fifth embodiment of the present invention. FIG. 34 is a plan view that shows the state of the leaves of FIG. 33 in the course of their movement.

In a diseased part of the patient's body, there is a portion which should not be subjected to irradiation, being located like an isolated island while being surrounded by the target 25 to be irradiated. Thus, upon such irradiation, it becomes necessary to provide a non-irradiation zone 36 in the target 25 to be irradiated, as shown in FIG. 33. For instance, it is the case where the dose to the spinal cord is desired to be reduced in the irradiation of the trunk of the body. In this case, by dividing the area to be irradiated into a first irradiation zone 26 and a second irradiation zone 27 astride the non-irradiation zone 36, irradiation can be made in an area surrounding the outer periphery of the non-irradiation zone 36 by using the control procedure as described in the first embodiment.

Such an irradiation apparatus can perform irradiation to the location to be irradiated, which is lying around a vital internal organ or radiation-sensitive internal organ such as the spinal cord, which is surrounded by the target and located like an isolated island.

Embodiment 6.

Figure 35:
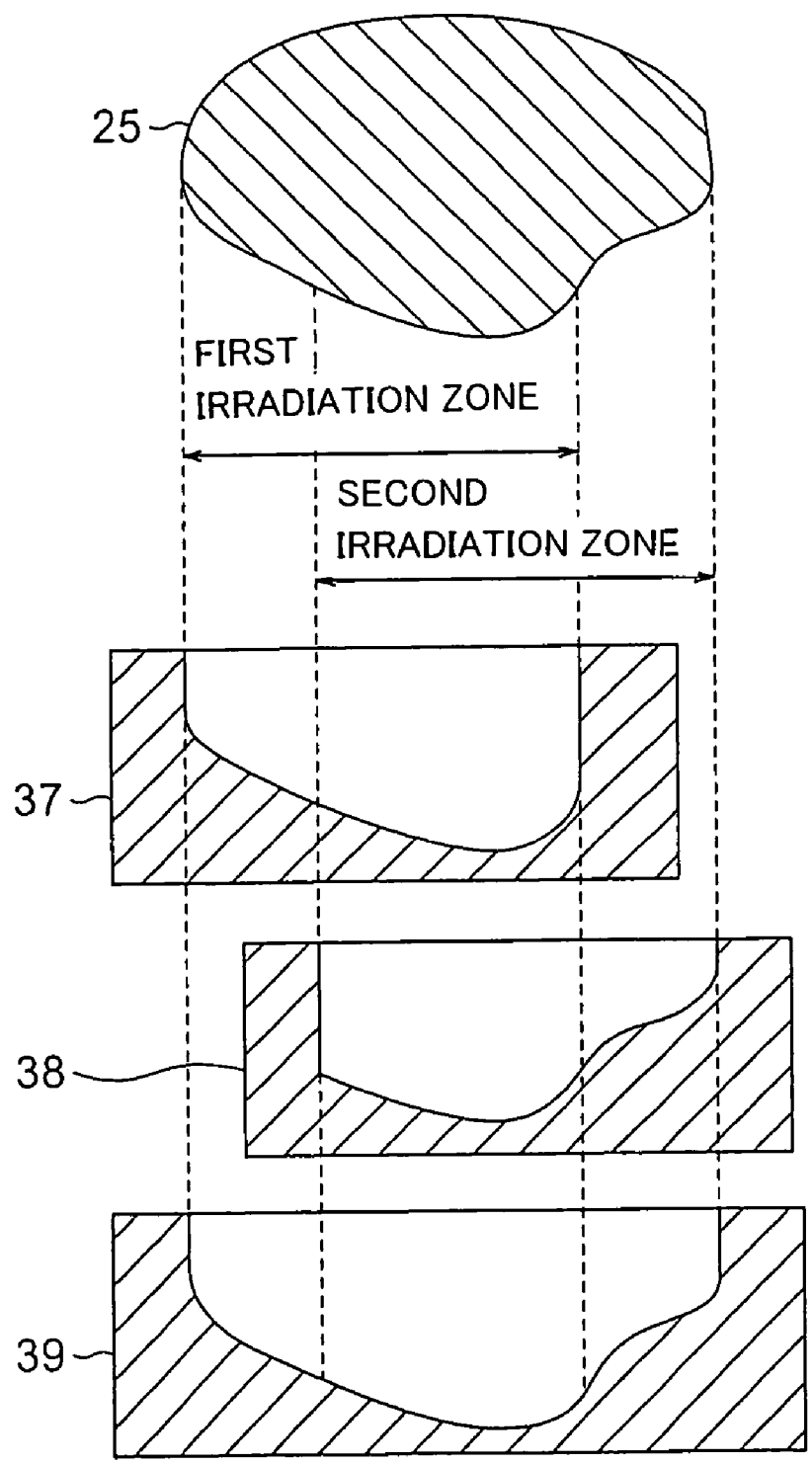
FIG. 35 is a cross sectional view of a compensating filter in an irradiation apparatus according to a sixth embodiment of the present invention.
Figure 37:
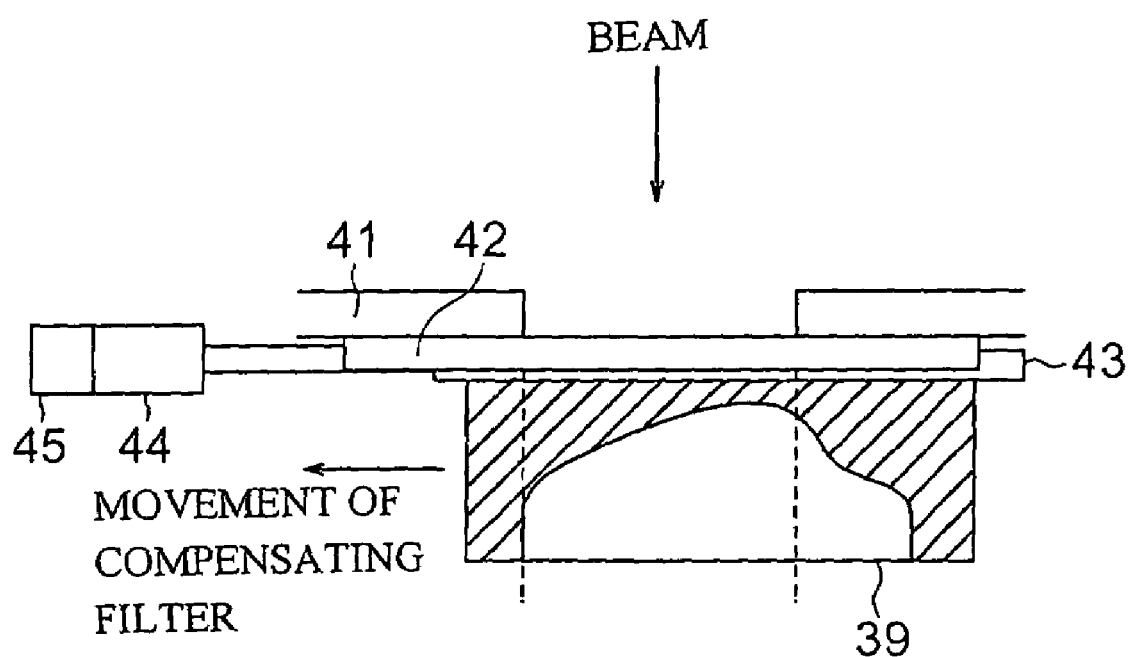
FIG. 37 is a cross sectional view of a drive unit for driving the compensating filters of FIG. 35 and a position reading mechanism.

FIG. 35 is a cross sectional view of a compensating filter in an irradiation apparatus according to the sixth embodiment of the present invention. FIGS. 36A through 36C are schematic views illustrating the movement of the compensating filter in FIG. 35, wherein FIGS. 36A and 36C show the different positional positions of the compensating filter with respect to an irradiation beam, and FIG. 36B is a cross sectional view taken along line A—A in FIG. 36A. FIG. 37 is a cross sectional view of a filter driving mechanism for moving the compensating filter of FIG. 35 and a filter position verification mechanism.

In the past, in order to irradiate an irradiation target 25 of a varying three-dimensional configuration, as shown in FIG. 35, compensating filters 37, 38 are prepared for a first irradiation zone and a second irradiation zone, respectively, and are replaced one with the other upon irradiation to each of the irradiation zones.

However, separate preparations of two kinds of compensating filters 37, 38 are costly, and the replacement work of the compensating filters 37, 38 has to be done during the irradiation, incurring the time and trouble of an operator.

Thus, the irradiation apparatus 6 according to the sixth embodiment includes a compensating filter 39 corresponding to the entire irradiation target 25, and a filter driving mechanism 40 for moving the compensating filter 39 so as to irradiate the second irradiation zone after irradiation of the first irradiation zone. The filter driving mechanism 40 is provided with a pair of rails 42 mounted to a multileaf collimator frame 41, a holder 43 being slidable along the rails 42 with the compensating filter 39 attached thereto, and a drive unit 44 for driving the holder 43. The drive unit 44 comprises a pulse motor, but it may be a well-known system such as a servo motor, an air cylinder, or the like.

Further, if a filter position verification mechanism 45 is attached to the filter driving mechanism 44 so as to automatically verify the position of the compensating filter 39 in each of the irradiation zones, it becomes a measure for prevention of mis-irradiation, thereby making it possible to improve the safety of the irradiation apparatus 6. The filter position verification mechanism 45 counts and administers the number of pulses of the drive unit 44 in the form of a pulse motor from the origin position so as to control the operation of the drive unit 44. Here, note that in cases where measurements are not made by a potentiometer or remote control is not made, there may be used a known system such as a position reading mechanism in which a plurality of latches are arranged in several stages on the mounting rails so that the position of the compensating filter can be read by the use of switches provided on the latches, respectively.

With such an irradiation apparatus, the two irradiation zones can be handled by moving only the single compensating filter to the right and left, as a result of which the manufacturing cost of the compensating filter can be reduced and the frequency of replacement thereof can be decreased as well, thereby alleviating the load on the part of the patient and operator.

Furthermore, provision of the filter driving mechanism serves to achieve improvements in the operation or manipulation at the time of replacement of the compensating filter as well as preventing the filter from falling around the patient.

In addition, provision of the filter position verification mechanism also serves to improve the safety against mis-irradiation.

In the above description, irradiation to the two irradiation zones have been carried out by the single common compensating filter, but when three or more irradiation zones are irradiated, it is similarly possible to accommodate these irradiation zones by a common single, or reduced number of, compensating filter(s).

As can be seen from the foregoing, the present invention provides the following advantages.

According to the present invention, there is provided an irradiation apparatus for irradiating a radiation beam transported from a particle accelerator onto a target to be irradiated that is positioned on an irradiation table. The irradiation apparatus includes: a beam interruption part for interrupting the radiation beam; a position control part for controlling the position of the irradiation table in such a manner that the radiation beam is irradiated onto the entire surface of the irradiation target in a plurality of irradiation zones including an overlapping zone formed by a plurality of irradiations of the radiation beam; and a multileaf collimator control part for controlling the radiation beam so as to provide a slope to the dose distribution in the overlapping zone of the respective irradiation zones such that the dose distribution is made flat over the entire surface of the target including the overlapping zone by the plurality of irradiations of the radiation beam. With this arrangement, it becomes possible to irradiate a wide location or area, and in such a case, an excellent or desired flatness of the dose distribution can be obtained with ease.

While the invention has been described in terms of preferred embodiments, those skilled in the art will recognize that the invention can be practiced with modifications within the spirit and scope of the appended claims.

What is claimed is:

1. An irradiation apparatus for radiating a radiation beam transported from a particle accelerator onto a location to be irradiated that is positioned on an irradiation table, said apparatus comprising:
   a beam interruption part for interrupting said radiation beam;
   a position control part for controlling a position of said irradiation table such that said radiation beam is radiated onto an entire surface of a target in a plurality of irradiation zones including an overlapping zone formed by a plurality of radiations of said radiation beam; and
   a multileaf collimator control part for controlling said radiation beam to provide a slope to a dose distribution in said overlapping zone of said irradiation zones, respectively, such that the dose distribution is made flat over the entire surface of said target including said overlapping zone by the plurality of radiations of said radiation beam.

2. The irradiation apparatus of claim 1, wherein said slope is approximated by a straight line.

3. The irradiation apparatus of claim 1, wherein said slope has different gradients and is approximated by two or more straight lines connected with each other.

4. The irradiation apparatus of claim 1, wherein said slope changes in a stepwise manner.

5. The irradiation apparatus of claim 1, wherein said slope is approximated by a curved line.

6. The irradiation apparatus of claim 1, wherein said multileaf collimator control part includes a multileaf collimator provided with a plurality of pairs of opposed leaves, and said multileaf collimator control part decreases a dose irradiated to said overlapping zone in a direction from a boundary between said overlapping zone and a non-overlapping zone toward another irradiation zone by moving at least one of said opposed leaves in each pair.

7. The irradiation apparatus of claim 6, wherein said multileaf collimator is operated by remote control.

8. The irradiation apparatus of claim 6, wherein a direction in which said leaves are driven to move is parallel to the direction in which said dose decreases.

9. The irradiation apparatus of claim 6, wherein a direction in which said leaves are driven to move is perpendicular to the direction in which said dose decreases.

10. The irradiation apparatus of claim 1, wherein said target encloses an area to which said radiation beam is not radiated.

11. The irradiation apparatus of claim 1, further comprising a compensating filter commonly usable with at least two of said irradiation zones, wherein when irradiation is changed from one of said irradiation zones to another a filter driving mechanism drives said compensating filter to move to a position suitable for irradiation.

12. The irradiation apparatus of claim 11, further comprising a filter position verification mechanism for verifying the position of said compensating filter.

13. The irradiation apparatus of claim 1, wherein said irradiation apparatus is incorporated in a radiotherapy system.

14. An irradiation method for radiating a charged particle beam transported from a particle accelerator onto a location to be irradiated that is positioned on an irradiation table, said method comprising:

dividing a location to be irradiated into a first irradiation zone and a second irradiation zone, the first irradiation zone and the second irradiation zone partially overlapping creating an overlapping zone;

radiating a radiation beam to said first irradiation zone such that a distribution of a dose radiated to said overlapping zone has a slope that decreases from a boundary between said overlapping zone and a non-overlapping zone of said first irradiation zone toward said second irradiation zone; and radiating a radiation beam to said second irradiation zone such that a distribution of a dose radiated to said overlapping zone has a slope that decreases from a boundary between said overlapping zone and a non-overlapping zone of said second irradiation zone toward said first irradiation zone, with a dose distribution in a target being made flat.

15. An irradiation method for radiating a charged particle beam transported from a particle accelerator onto a location to be irradiated that is positioned on an irradiation table, said method comprising:

dividing a location to be irradiated into first, second, and third irradiation zones that partially overlap, each of the first, second, and third irradiation zones having non-overlapping zones and overlapping zones adjoining each other;

radiating a radiation beam to said first irradiation zone such that a distribution of a dose radiated to two overlapping zones in said first irradiation zone overlapping with at least one of said second irradiation zone and said third irradiation zone has a slope that decreases from boundaries between said overlapping zones and a non-overlapping zone in said first irradiation zone toward at least one of said second and third irradiation zones;

radiating the radiation beam to said second irradiation zone in such a manner that a distribution of a dose radiated to two overlapping zones in said second irradiation zone overlapping with at least one of said first and third irradiation zones has a slope that decreases from boundaries between said overlapping zones and a non-overlapping zone in said second irradiation zone toward at least one of said first and third irradiation zones, with a total dose distribution in said overlapping zone of said second irradiation zone that overlaps with said first irradiation zone alone being made flat; and radiating the radiation beam to said third irradiation zone in such a manner that a distribution of a dose radiated to two overlapping zones of said third irradiation zone overlapping with at least one of said first and second irradiation zones has a slope that decreases from boundaries between said overlapping zones and a non-overlapping zone in said third irradiation zone toward at least one of said first and second irradiation zones, with a total dose distribution in said overlapping zones of said third irradiation zone that overlap with one of said first and second irradiation zones being made flat.

* * * * *